United States Patent
Norman et al.

(10) Patent No.: US 10,702,605 B2
(45) Date of Patent: *Jul. 7, 2020

(54) CO-PROCESSED CARBOHYDRATE SYSTEM AS A QUICK-DISSOLVE MATRIX FOR SOLID DOSAGE FORMS

(71) Applicant: SPI Pharma, Inc., Wilmington, DE (US)

(72) Inventors: Gary T. Norman, Middletown, DE (US); Kalyan S. Nuguru, Mantua, NJ (US); Arun F. Amin, Wilmington, DE (US); Sarath Chandar, Moorestown, NJ (US)

(73) Assignee: SPI Pharma, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/840,232

(22) Filed: Aug. 31, 2015

(65) Prior Publication Data

US 2016/0051680 A1 Feb. 25, 2016

Related U.S. Application Data

(63) Continuation of application No. 14/038,924, filed on Sep. 27, 2013, now Pat. No. 9,138,413, which is a continuation of application No. 11/448,523, filed on Jun. 6, 2006, now Pat. No. 8,545,889, which is a continuation of application No. 10/274,227, filed on Oct. 18, 2002, now Pat. No. 7,118,765.

(60) Provisional application No. 60/341,366, filed on Dec. 17, 2001.

(51) Int. Cl.
| | |
|---|---|
| *A61K 9/00* | (2006.01) |
| *A61K 9/20* | (2006.01) |
| *A61K 47/26* | (2006.01) |
| *A61K 9/16* | (2006.01) |
| *A61K 31/137* | (2006.01) |
| *A61K 31/167* | (2006.01) |
| *A61K 31/439* | (2006.01) |
| *A61K 31/485* | (2006.01) |

(52) U.S. Cl.
CPC .......... *A61K 47/26* (2013.01); *A61K 9/0056* (2013.01); *A61K 9/1694* (2013.01); *A61K 9/2018* (2013.01); *A61K 9/2081* (2013.01); *A61K 31/137* (2013.01); *A61K 31/167* (2013.01); *A61K 31/439* (2013.01); *A61K 31/485* (2013.01)

(58) Field of Classification Search
None
See application file for complete search history.

(56) References Cited

U.S. PATENT DOCUMENTS

| | | | |
|---|---|---|---|
| 3,145,146 A | 8/1964 | Lieberman et al. | |
| 4,605,794 A | 8/1986 | Reiff et al. | |
| 4,990,537 A | 2/1991 | Okuyama et al. | |
| 5,382,434 A | 1/1995 | de Haan et al. | |
| 5,464,632 A | 11/1995 | Cousin et al. | |
| 5,489,439 A | 2/1996 | Bola | |
| 5,573,777 A | 11/1996 | Serpelloni et al. | |
| 5,576,014 A | 11/1996 | Mizumoto et al. | |
| 5,583,215 A | 12/1996 | Kawashima et al. | |
| 5,635,210 A * | 6/1997 | Allen, Jr. ............ | A61K 9/0056 264/13 |
| 5,720,974 A | 2/1998 | Makino et al. | |
| 5,958,471 A | 9/1999 | Schwarz et al. | |
| 6,024,981 A | 2/2000 | Khankari et al. | |
| 6,106,861 A | 8/2000 | Chavreau et al. | |
| 6,114,369 A | 9/2000 | Tanikawa et al. | |
| 6,149,941 A | 11/2000 | Schwarz et al. | |
| 6,165,511 A * | 12/2000 | Schwarz ............ | A61K 9/0056 424/440 |
| 6,221,392 B1 | 4/2001 | Khankari et al. | |
| 6,248,359 B1 | 6/2001 | Faour | |
| 6,274,727 B1 * | 8/2001 | Maul .................... | A23G 3/0242 127/15 |
| 6,284,270 B1 | 9/2001 | Lagoviyer et al. | |
| 6,395,893 B1 * | 5/2002 | Heikkila ................ | C07H 15/04 426/660 |
| 6,814,978 B2 | 11/2004 | Bunick et al. | |
| 6,998,482 B2 | 2/2006 | Erdmann et al. | |
| 7,118,765 B2 | 10/2006 | Norman et al. | |
| 8,545,889 B2 | 10/2013 | Norman et al. | |
| 2002/0071864 A1 | 6/2002 | Kim et al. | |
| 2002/0114833 A1 | 8/2002 | Abu-Izza et al. | |
| 2004/0071772 A1 | 4/2004 | Narita et al. | |
| 2004/0121006 A1 | 6/2004 | Narita et al. | |
| 2014/0023707 A1 | 1/2014 | Norman et al. | |

FOREIGN PATENT DOCUMENTS

| | | |
|---|---|---|
| EP | 0738252 B1 | 5/1996 |
| EP | 0839526 A2 | 5/1998 |
| EP | 0839526 A3 | 1/1999 |
| EP | 0960621 A2 | 1/2000 |
| EP | 0960621 A3 | 1/2000 |
| EP | 0896528 B1 | 12/2001 |
| EP | 1203580 A1 | 5/2002 |

(Continued)

OTHER PUBLICATIONS

Opposition dated Apr. 11, 2014 filed in European Patent No. EP1465604.

(Continued)

*Primary Examiner* — Susan T Tran

(74) *Attorney, Agent, or Firm* — Morgan, Lewis & Bockius LLP

(57) ABSTRACT

The present invention comprises a co-processed carbohydrate system, and formulations produced therefrom, which formulations are directly compressible into solid dosage forms, some of which rapidly and completely dissolve or disintegrate in the oral cavity within 60 seconds. The invention also comprises the solid dosage forms produced by directly compressing the co-processed carbohydrate system, some of which, when placed in the oral cavity, shall dissolve or disintegrate, preferably within about 60 seconds.

20 Claims, 25 Drawing Sheets

(56) References Cited

FOREIGN PATENT DOCUMENTS

| EP | 1369109 | 12/2003 |
|---|---|---|
| EP | 1369131 | 12/2003 |
| WO | 8701936 A1 | 4/1987 |
| WO | 9614282 A1 | 5/1996 |
| WO | 9739739 A2 | 10/1997 |
| WO | 9741835 A1 | 11/1997 |
| WO | 9822094 A2 | 5/1998 |
| WO | 9846215 A1 | 10/1998 |
| WO | 9918935 A1 | 4/1999 |
| WO | 9958704 A1 | 11/1999 |
| WO | 0057857 A1 | 10/2000 |
| WO | 0076650 A1 | 12/2000 |
| WO | 0215880 A2 | 2/2002 |
| WO | 03055834 A2 | 7/2003 |

OTHER PUBLICATIONS

Bauer et al. "Particle design by surface modifications: spray-drying and co-granulation of mannitol/sorbitol mixtures."S.T.P. Pharma Sciences 11 (3) 203-209 (2001).

FMC BioPolymer Ac-Di-Sol [online]. FMC Corporation [retrieved on Apr. 1, 2014]. Retrieved from the Internet: <URL: http://www.fmcbiopolymer.com/Pharmaceutical/Products/AcDiSol.aspx>.

Glidant [online]. Wikipedia [retrieved on Apr. 1, 2014]. Retrieved from the Internet: <URL: http://en.wikipedia.org/wiki/Glidant>.

\* cited by examiner

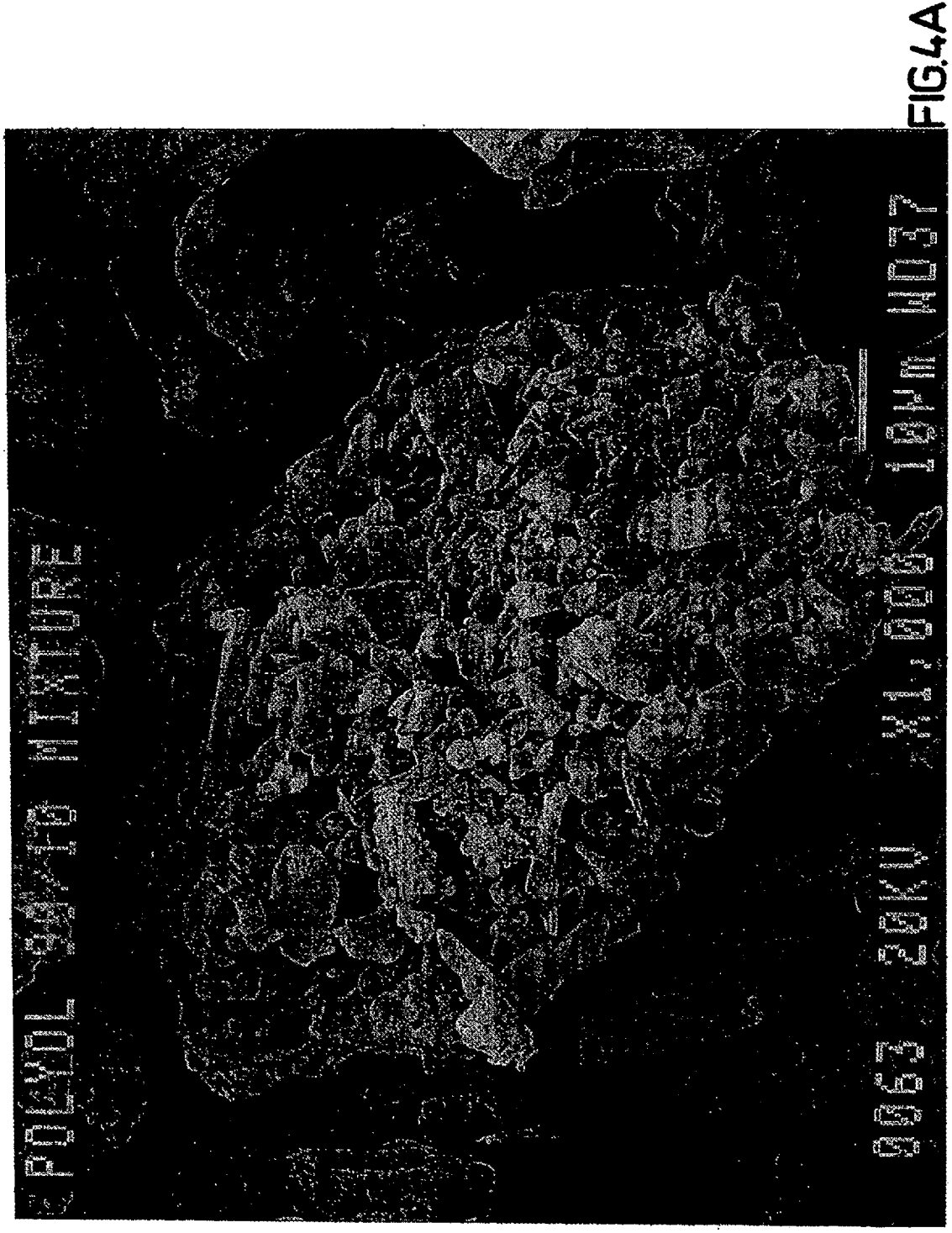

CO-PROCESSED CARBOHYDRATE SYSTEM AS A QUICK-DISSOLVE MATRIX FOR SOLID DOSAGE FORMS

CROSS-REFERENCE TO RELATED APPLICATIONS

This application is a continuation of U.S. application Ser. No. 14/038,924, filed Sep. 27, 2013, which is a continuation of U.S. application Ser. No. 11/448,523, filed Jun. 6, 2006 (now U.S. Pat. No. 8,545,889), which is a continuation of U.S. application Ser. No. 10/274,227, filed Oct. 18, 2002 (now U.S. Pat. No. 7,118,765), which claims priority to U.S. Provisional Application No. 60/341,366, filed Dec. 17, 2001, all of which are incorporated herein by reference in their entirety.

FIELD OF THE INVENTION

The present invention relates to co-processed carbohydrate systems that produce formulations that are directly compressible into solid dosage forms, some of which rapidly and completely dissolve and/or disintegrate in the oral cavity, preferably within about 60 seconds. The invention also relates to solid dosage forms produced by directly compressing a co-processed carbohydrate system, along with other ingredients, some of which when placed in the oral cavity, dissolves or disintegrates, preferably within about 60 seconds.

The present invention also relates to co-processed carbohydrates that produce formulations that are directly compressible into solid dosage forms, which formulations, when co-processed, form particles having a non-filamentous microstructure.

BACKGROUND OF THE INVENTION

U.S. Pat. No. 6,221,392 which was issued on Apr. 24, 2001 and U.S. Pat. No. 6,024,981 which was issued on Feb. 15, 2000 both to Khankari et al., describe a hard tablet that is said to dissolve rapidly in the mouth of the patient with a minimum of grit. The tablet is created from an active ingredient mixed into a matrix of a nondirect compression filler and a relatively high lubricant level.

U.S. Pat. No. 5,576,014 which was issued on Nov. 19, 1996 to Mizumoto et al., describes intrabuccally dissolving compressed moldings including a saccharide having low moldability having been granulated with a saccharide having high moldability. The moldings are said to show quick disintegration and dissolution in the buccal cavity and have an adequate hardness.

U.S. Pat. No. 5,720,974 which was issued on Feb. 24, 1998 to Mikano et al., describes a method of producing a fast dissolving tablet including compression-molding a composition having an active ingredient, a carbohydrate and a barely sufficient amount of water to moisten the surface of particles of the carbohydrate into a tablet form and a fast dissolving tablet obtainable by the method. The active ingredient may, for example, be a vitamin, a gastrointestinal function conditioning agent or an anti-pyretic-analgesic-anti-inflammatory agent. The carbohydrate includes, but is not limited to sugar, starch, lactose, honey, sugar alcohols and tetroses. The amount of water to be added is about 0.3% to 10% by weight. The fast dissolving tablet is said to have a porous structure with excellent disintegratability and solubility as well as adequate strength.

U.S. Pat. No. 5,958,471, which was issued on Sep. 28, 1999 to Schwarz, et al., describes a spray-dried composition including two or more polyols, such as sorbitol, mannitol, and xylitol, where mannitol is present in a quantity less than 10 percent by weight.

U.S. Pat. No. 6,165,511, which was issued on Dec. 26, 2000 to Schwarz, et al., describes a process for preparing a spray-dried composition including a polyol. The process includes preparing an aqueous solution of more than 80% of one or more non-hygroscopic polyols and spraying the resulting mixture into an air stream. The resulting composition of the spray-drying process contains a filamentous structure.

International Publication No. WO00/57857 (PCT/KR00/00242), published Oct. 5, 2000, to Yuhan Corporation discloses a rapidly disintegrable tablet which includes an active ingredient, spray-dried mannitol, crospovidone, and at least one pharmaceutically acceptable excipient. Other additives, such as a lubricant and a sweetening agent may also be included in the tablet composition.

All patents referenced in this application are herein incorporated by reference in their entirety.

BRIEF SUMMARY OF THE INVENTION

In one embodiment, the present invention relates to a method for producing a directly compressible composition having a nonfilamentous microstructure, preferably that quickly dissolves in the buccal cavity in less than 60 seconds. The present invention also relates to a method for producing a quick-dissolving composition. Compositions prepared from the methods taught herein are also described. Finally, tablets prepared from the compositions are disclosed.

In one embodiment the present invention includes a method for producing a directly compressible and highly compactible composition.

In one embodiment of the method of the invention, the method includes dissolving mannitol powder and sorbitol powder into a solution, drying the solution in an air stream, and forming a composition that completely dissolves in the oral cavity within about 60 seconds.

In one embodiment of the method of the invention, the method includes dissolving mannitol powder and sorbitol powder into a solution, drying the solution in an air stream, and forming a particle having a nonfilamentous microstructure from the solution.

In another embodiment of the method of the present invention, the method includes dissolving mannitol powder and sorbitol powder into a solution, drying the solution in an air stream, forming a particle having a nonfilamentous microstructure from the solution, and forming a composition that completely dissolves in the oral cavity, preferably within about 60 seconds.

In an embodiment of the method of the present invention, the method produces a composition having a moisture content of less than about 8%. Preferably, the moisture content is less than about 5%, and more preferably, less than about 2%.

In another embodiment of the method of the present invention, the method includes adding a disintegrant to the composition. In one embodiment, the disintegrant is selected from crospovidone, croscarmellose, sodium starch glycolate, or combinations thereof.

In one embodiment of the method of the present invention, the method also includes adding a glidant to the composition. In one embodiment, the glidant is selected from colloidal silica, silica gel, precipitated silica, or combinations thereof.

In one embodiment of the method of the present invention, an active ingredient is added to the composition. The active ingredient is coated or uncoated.

In another embodiment of the method of the present invention, the range of mannitol present in the solution is from about 60% to about 99.5%, preferably about 70% to 95%, and more preferably about 80% to 90%. The range of sorbitol present in the solution is from about 0.5% to 40%, preferably about 5% to 30%, and more preferably about 10% to 20%.

In another embodiment of the method of the present invention, the method includes dry feeding a blend of dry mannitol powder and sorbitol powder into the spray-drying chamber.

In another embodiment of the method of the present invention, the method includes diluting the resulting composition with a dry mixture of mannitol and a disintegrant. In one embodiment, the disintegrant is selected from croscarmellose, crospovidone, or sodium starch glycolate, or mixtures thereof. In another embodiment, the dry mixture includes about 90% mannitol and about 10% disintegrant.

In another embodiment of the method of the present invention, the method includes forming a tablet from the resulting composition.

In another embodiment of the present invention, a quick-dissolving composition having at least co-spray-dried mannitol and sorbitol and a disintegrant is also described. In an embodiment, the mannitol is present in a range of from about 60 to about 99.5 percent and said sorbitol is present in a range of from about 0.5 to about 40 percent of the co-spray dried material. In another embodiment, the range of mannitol is about 70% to 95% and the range of sorbitol is about 5% to 30%. In another embodiment, the range of mannitol is about 80% to 90% and the range of sorbitol is about 10% to 20%. The quick-dissolving composition can be directly compressible.

In another embodiment of the composition of the present invention, the composition further includes a glidant. In one embodiment, the glidant is selected from colloidal silica, silica gel, precipitated silica, or combinations thereof.

In another embodiment, the composition further includes at least one active ingredient. In one embodiment, the active ingredient is coated. In another embodiment, the active ingredient is not coated. In another embodiment, the composition includes coated and uncoated active ingredients.

In one embodiment of the present invention, the composition further includes one or more disintegrating agents. The disintegrating agent includes crospovidone, croscarmellose, sodium starch glycolate, or combinations thereof.

In another embodiment of the present invention, the composition is highly compactible and includes particles having a nonfilamentous microstructure including co-spray dried mannitol and sorbitol. In one embodiment, the mannitol is present in a range of from about 60 to about 99.5 percent and said sorbitol is present in a range of from about 0.5 to about 40 percent of the co-spray dried material. In another embodiment, the range of mannitol is about 70% to 95% and the range of sorbitol is about 5% to 30%. In another embodiment, the range of mannitol is about 80% to 90% and the range of sorbitol is about 10% to 20%. The quick-dissolving composition can be directly compressible.

The invention also encompasses tablets comprising any of the compositions of the present invention.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings preferred embodiment(s). It should be understood, however, that the invention is not limited to the precise arrangements and instrumentalities shown. In the drawings:

FIG. 4A is a scanning electron micrograph (SEM) of Formulation A after it is dried in the spray dryer (magnification 1000×).

FIG. 5A represents an SEM (magnification 100×) of spray-dried mannitol produced by SPI Pharma, Inc. (New Castle, Del.). The moisture was measured to be 1.0% KF (as measured by Karl Fischer (KF) AF8).

FIG. 5B represents FIG. 5A at 1000× magnification.

FIG. 5C represents an SEM (magnification 100×) of mannitol produced by Cerestar (France). The moisture was 0.96% KF FIG. 5D represents FIG. 5C at 1000× magnification.

FIG. 5E represents an SEM (magnification 100×) of mannitol produced by GETEC (Brazil). The moisture was 0.82% KF FIG. 5F represents FIG. 5E at 1000× magnification.

FIG. 5G represents mannitol produced by SPI Pharma, Inc., as in FIG. 5A (magnification 100×); however, the mannitol in FIG. 5G is seeded with dry mannitol particles during the drying process. The moisture was 0.33% KF.

FIG. 5H represents FIG. 5G at 1000× magnification.

FIG. 9A represents the particle morphology at 100× magnification; FIG. 9B represents the particle morphology at 1000× magnification; FIG. 9C represents the particle morphology at 2000×. No filamentous structure on the particles is observed.

FIG. 10A represents the particle morphology at 100× magnification; FIG. 10B represents the particle morphology at 1000× magnification; FIG. 10C represents the particle morphology at 2000×. No filamentous structure on the particles is observed.

Figure 1:
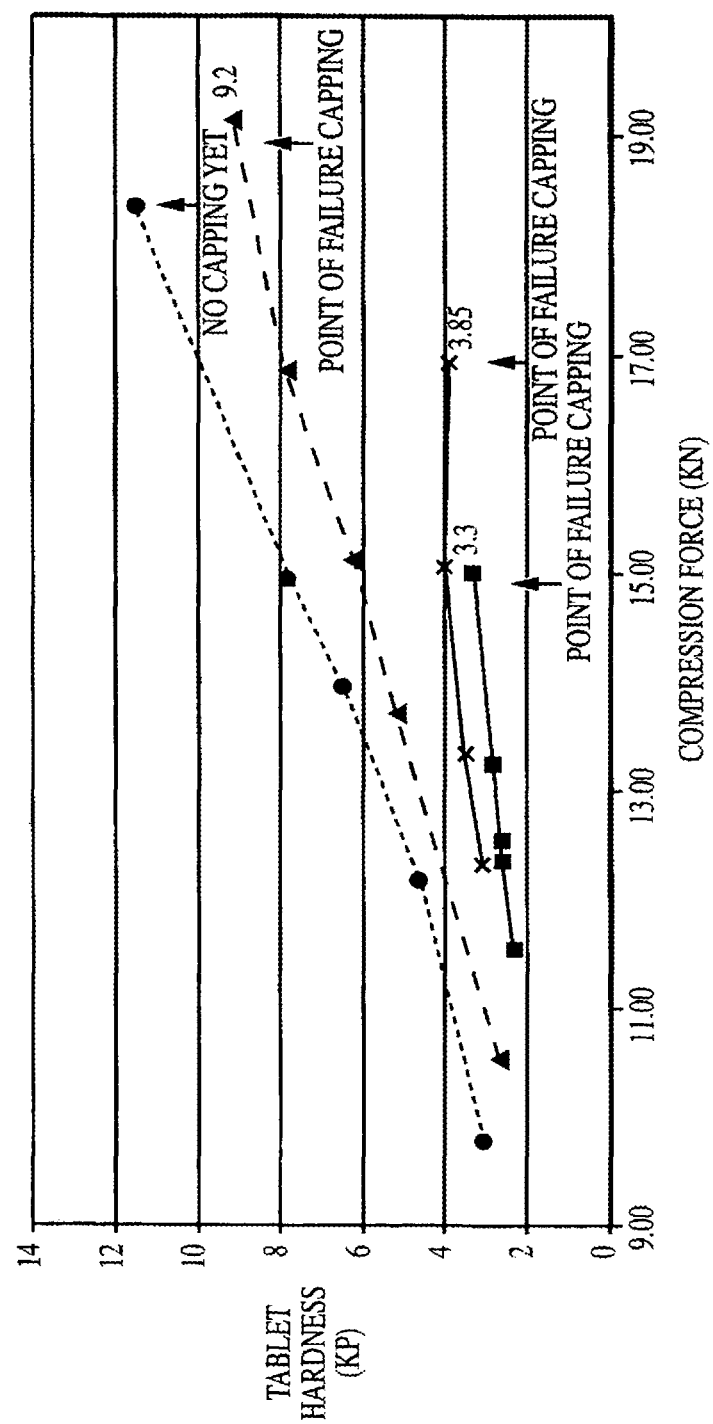
FIG. 1 is a graph depicting tablet hardness versus compaction force for each of Formulation A (triangle), Formulation B (square), Formulation C ("x"), and Formulation D (circle).

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

The present invention includes quick dissolving solid dosage forms produced from quick dissolving formulations including a co-processed carbohydrate system. In one embodiment, the solid dosage forms of the present invention are prepared by direct compression. The solid dosage forms rapidly dissolve or disperse in the oral cavity of a patient, thus releasing any active ingredient contained within the formulation.

The present invention also includes a co-processed carbohydrate system, and formulations produced therefrom that are directly compressible into solid dosage forms which rapidly and completely dissolve and/or disintegrate in the oral cavity, preferably within about 60 seconds.

The present invention also includes co-processed carbohydrates, and formulations produced therefrom, which co-processed carbohydrates and formulations comprise particles having a non-filamentous microstructure. The co-processed carbohydrates and the formulations produced therefore are directly compressible into solid dosage forms.

The present invention is described herein using several definitions, as set forth below and throughout the application.

Definitions

The term "about" will be understood by persons of ordinary skill in the art and will vary to some extent on the context in which it is used. If there are uses of the term which are not clear to persons of ordinary skill in the art given the context in which it is used, "about" shall mean up to plus or minus 10% of the particular value.

The phrase "completely dissolve or disintegrate" used in the context of the present invention, means that the solid dosage form dissolves or disintegrates to an extent that the patient believes the solid dosage form to be completely dissolved or disintegrated. That is, the patient can no longer detect any significant lumps or large particles of the original solid dosage form. Instead, at the point in time when the solid dosage from has completely dissolved or disintegrated in the oral cavity of the patient, the solid dosage form preferably has a creamy and pleasant mouthfeel that is conducive to swallowing.

The terms "solid dosage form," "tablet," and "solid preparation" are used synonymously within the context of the present invention. These terms should be construed to include a compacted or compressed powder composition obtained by compressing or otherwise forming the composition to form a solid having a defined shape.

The term "directly compressible" means that the composition can be compressed to tablet form on standard tableting machines (including, but non limited to high speed tableting machines) using standard (i.e., without any specially machined, shaped or coated surfaces) punches and dies, without any significant amount of the composition adhering to the punches and dies.

The term "oral cavity" should be construed to include, but should not be limited to the buccal cavity.

The term "co-processed carbohydrate" means the processing of at least two polyols together to make a single product. For example, mannitol and sorbitol may be co-spray dried by first preparing a single solution of mannitol and sorbitol. Another example includes the co-granulation of mannitol and sorbitol.

The term "co-processed carbohydrate system" shall be construed to include a co-processed carbohydrate plus a disintegrant and a glidant.

The term "co-processed carbohydrate system formulation or composition" shall be construed to include the co-processed carbohydrate system plus an active ingredient to be formed into a tablet.

It has been discovered that the existing processes, products, or systems directed towards rapid disintegration or dissolution in the mouth have limitations in certain aspects. Specifically, until now it has been difficult to produce a tablet that is robust (e.g., low friability, low ejection forces, sufficient hardness) enough to be processed in high speed tableting machines and shipped in low cost packages, and at the same time retain rapid disintegration or dissolution properties. This is especially obvious when producing a tablet having high doses of active ingredients (AIs) or when producing a tablet having AIs coated with different polymers, waxes, and the like for taste-masking purposes.

An advantage of the formulations of the present invention is that they can be formed into high quality tablets on standard tableting machines (including high speed tableting machines such as those made by Killian or Korsh, capable of producing at least 75,000 tablets per hour) using standard punches and dies. The "standard" punches and dies referred to above are far less expensive to produce and maintain than the coated (e.g., teflon-coated) punches and dies used to produce tablets from formulations that are sticky or difficult to compress.

In one embodiment, the present invention overcomes these limitations by utilizing a co-processing technology that ultimately produces a formulation that is compressible into a tablet. This tablet is robust enough to withstand stress of handling during production, packaging and transportation, without special processing or handling, while retaining rapid disintegration or dissolution properties, in the oral cavity.

In one embodiment, a co-processed carbohydrate system formulation according to the present invention includes, but is not limited to at least two co-processed carbohydrates, one or more disintegrating agents, and one or more glidants. It is thought that the co-processed carbohydrate is the ingredient of the formulation that provides compactibility of the composition and a pleasant mouthfeel to the patient. The disintegrating agent aids in achieving maximal rapid disintegration of the solid dosage form. Finally, the glidant functions as an anti-caking agent and flow aid, and also aids in minimizing adherence of the individual materials of the formulation to the punches and dies of the tableting machinery.

Co-processing of carbohydrates includes, but is not limited to co-granulating at least two granular or crystalline polyols, co-granulating at least two spray-dried polyols, or co-granulating a spray dried polyol and a granular or crystalline polyol. Co-processing also includes, but is not limited to co-spray drying at least two polyols.

Carbohydrates useful in the present invention include, but are not limited to polyols, which are sugar alcohols of the general formula $CH_2OH—(CHOH)_n—CH_2OH$, where n is 2 to 6, and preferably 3 to 6, and their dimeric anhydrides. Preferably, the polyols include, but are not limited to sorbitol, mannitol, erythritol, maltitol, lactitol, isomalt, and mixtures thereof, and sugars such as lactose, fructose, dextrose, sucrose, maltose, and mixtures thereof.

In one embodiment of the present invention, a co-processed carbohydrate system formulation is prepared using mannitol and sorbitol as the carbohydrates as follows. First, mannitol is prepared from a 55 percent high fructose corn syrup, which is hydrogenated by feeding the syrup into an autoclave in the presence of a catalyst. The liquid obtained from this hydrogenation step is a mixture of about 40 percent mannitol and about 60 percent sorbitol. The mannitol is crystallized out of liquid solution by chilling the solution, and the mannitol is collected using centrifugation. The precipitated mannitol is then transferred to a belt for washing and then dried to form a powder mannitol. Typically, the prepared mannitol powder contains about 98 percent mannitol and up to about 2 percent sorbitol.

The prepared mannitol powder, and a sorbitol powder are then dissolved in hot water to form a solution, and the temperature of the solution is maintained at about 80 to 85 degrees Celsius. The ratio of mannitol to sorbitol can vary. In one embodiment, the mannitol:sorbitol ratio ranges from about 99.5:0.5 to about 60:40. In one embodiment, the ratio of mannitol to sorbitol is about 99.5:0.5. In another embodiment, the ratio of mannitol to sorbitol is about 90:10. In another embodiment, the ratio of mannitol to sorbitol is about 80:20. In another embodiment, the ratio of mannitol to sorbitol is 88:12, and in a separate embodiment the ratio of mannitol to sorbitol is 92:8. In another embodiment, the ratio of mannitol to sorbitol is about 60:40. Preferably, the mannitol content is equal to or higher than the sorbitol content.

At this point, the polyol composition is spray-dried. Any spray dryer is useful in the present invention. In one embodiment of the invention, an 51 Spray Fluid Bed Dryer with a 2.1 meter diameter is used (DRYTEC; Tonbridge, Kent, ENGLAND). The spray dryer operates by atomizing the liquid feed material (the co-processed polyol composition) in a stream of air or other gas. The main use of the spray drying equipment is drying but the equipment can also be used for agglomerating, congealing, encapsulation, cooling and/or conditioning the composition of the present invention. A flow diagram depicting the operation pattern of the fluid bed spray dryer is shown in FIG. 6.

Figure 6:
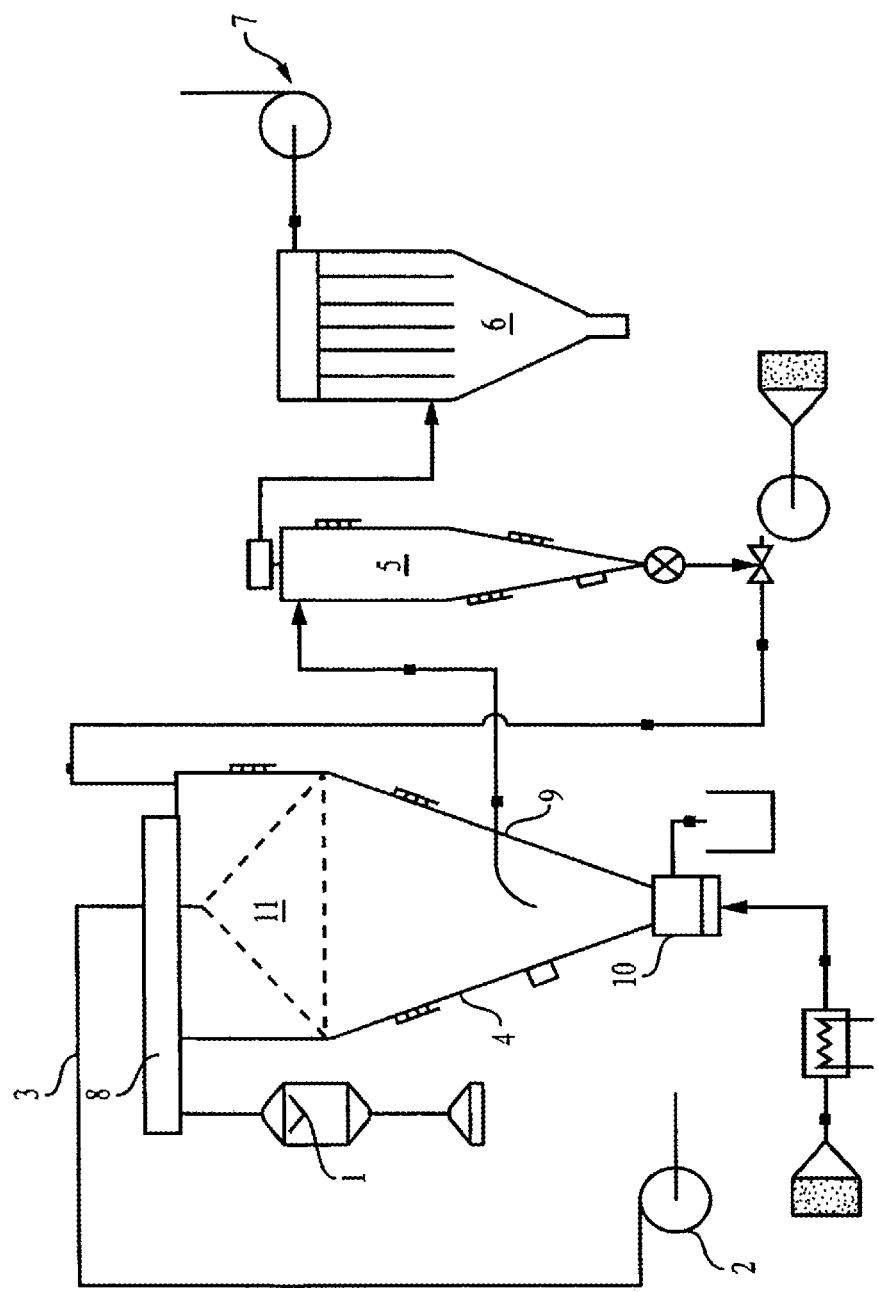
FIG. 6 is a flow diagram depicting a process for co-sprayed fluid-bed spray drying.

Referring to FIG. 6, air for drying is heated by a heater 1 and enters the top of a drying chamber 4 through a hot air duct 8. A feed pump 2 delivers the liquid feed through feed line 3 to an atomizer which sprays the composition in fine droplets into a hot air stream entering the top of a drying chamber 4. This causes rapid drying due to the large liquid area exposed. In the present invention, one of several atomizers can be used. For example, a centrifugal driven atomizer, a two fluid nozzle using a jet of compressed air to atomize the feed, or a pressure nozzle atomizer can be used in the present invention.

An integrated fluid bed 10 is attached at the bottom of chamber 4. The fines and air leave from a side outlet 9 of the cone of drying chamber 4 to a cyclone 5. Cyclone 5 separates the fines from the air. The air is exhausted out through a bag filter 6. The fines are recycled to the top of drying chamber 4 into a wet zone 11 where agglomeration takes place, and drop into integrated fluid bed 10. The action of the fluidization by the hot air supplied to the fluid bed allows the coarser particles to dry further and the fines are taken away to cyclone 5.

The polyol solution is then fed into the integrated spray fluid bed drying chamber unit under sealed conditions and a controlled stream of hot air at a temperature of about 200 degrees Celsius dries the solution in the form of fine droplets. Once the desired particle size is achieved, the polyol (mannitol/sorbitol) product is collected. Particle size can range from about 0.1 to 500 microns. In one embodiment of the present invention, at least 85 percent of the particles are about 100 microns or greater. In another embodiment of the present invention, at least 50 percent of the particles are about 100 microns or greater. The smaller particles ("fines") generated during this process are recycled back to the top of drying chamber 4 for further agglomeration.

The moisture content of the resulting co-processed polyol particle is preferably less than about 8%, and even more preferably, less than about 5%, and even more preferably, the moisture content is less than 2%. In one embodiment of the present invention, the moisture content of the resulting particle is about 0.3%.

Figure 4B:
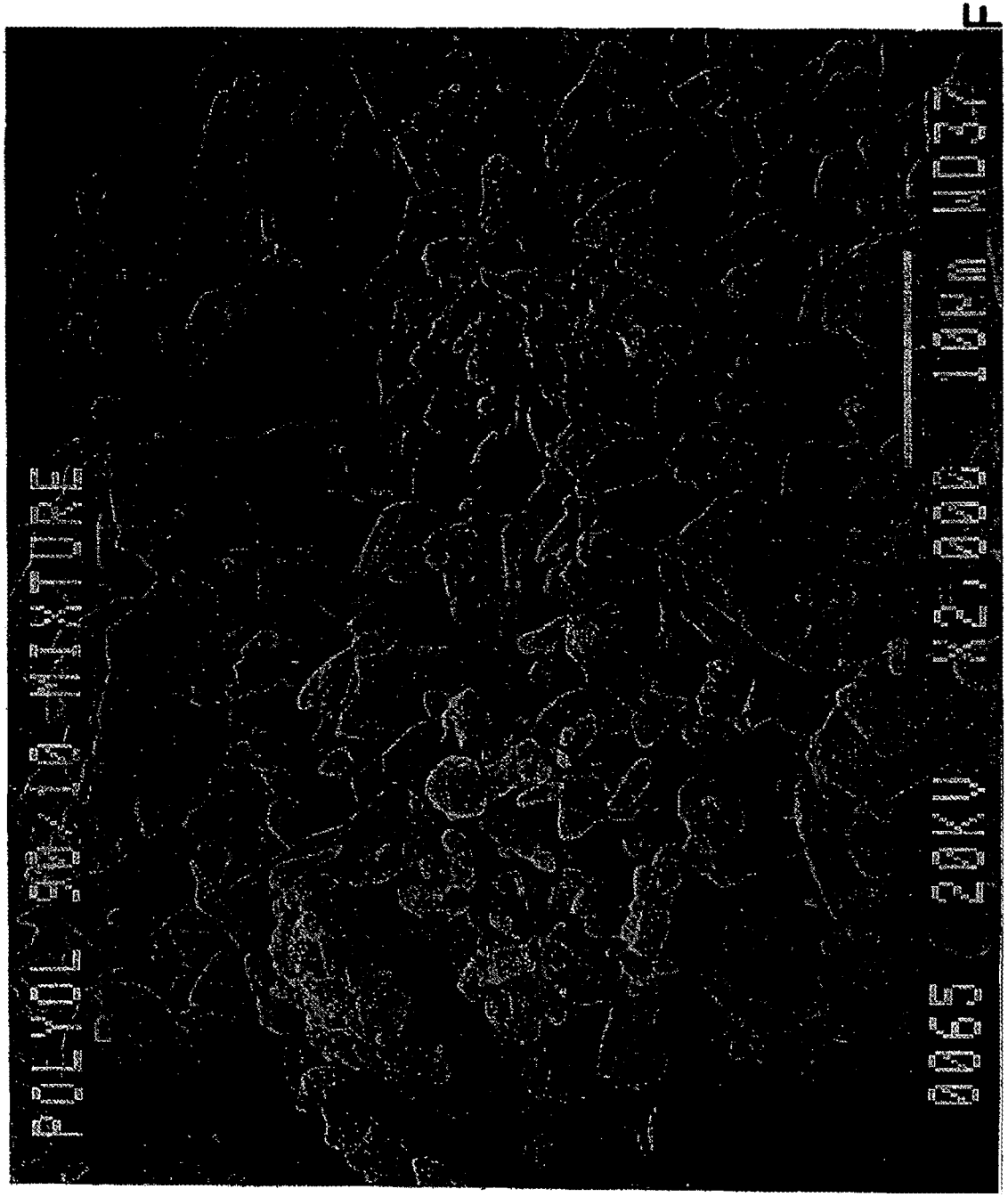
FIG. 4B is a 2000× magnification of the SEM in FIG. 4A.

As shown in FIGS. 4A and 4B, the final co-spray dried polyol composition has an irregular and globular or crystalline-like structure when examined under scanning electron microscopy.

The final co-spray dried polyol composition may have a surface shape (i.e., smooth surface, spherical in nature, with agglomerated particles) as depicted in the SEMs in FIGS. 5A-5F.

In one embodiment of the present invention, the co-processed mannitol:sorbitol ratio may be diluted after the co-spray drying process with a percentage of a co-granulated blend of mannitol and a disintegrant. Preferably, the co-processed mannitol:sorbitol ratio is diluted with up to about 50% of a co-granulated blend of about 90% MANNOGEM EZ™ (SPI Pharma, Inc., New Castle, Del.) and/or about 10% POLYPLASDONE-XL™ (ISP Technologies, Wayne, N.J.). Preferably, the co-processed mannitol:sorbitol is diluted with about 20% to 40% of the co-granulated blend of MANNOGEM EZ™ and/or POLYPLASDONE-XL™. In another embodiment, the co-processed mannitol:sorbitol is diluted with about 20% of the co-granulated blend of MANNOGEM EZ™ and POLYPLASDONE-XL™, and in another embodiment, the co-processed mannitol:sorbitol is diluted with about 40% of the co-granulated blend of MANNOGEM EZ™ AND POLYPLASDONE-XL™.

In one preferred embodiment of the present invention, the spray-dried mannitol/sorbitol polyol composition may first be seeded with dry particles of mannitol/sorbitol in the same proportion as the aqueous solution prepared for co-spray drying. Referring to FIG. 6, the dry particles are introduced into the fines recycle system of the spray dryer. In one embodiment, this is achieved using a vibratory feeder which is positioned at the inlet to a fines recycle fan 7. The dry particles are blended in a ribbon blender prior to loading the vibratory feeder. It is thought that introducing the dry particles into the fines recycle system may be advantageous in decreasing the moisture level of the final product.

The introduction of dry particles and/or the decrease in moisture level lead to a difference in morphology of the resulting co-spray dried particle. As shown in FIGS. 5G and 5H, the co-spray dried polyol composition that is first seeded with dry particles has a spherical particle shape without a filamentous structure on the surface, and has a decreased moisture content, from about 1% to about 0.3% of the particle weight. It is hypothesized that the lack of filamentous structure on the spherical particle shape may increase the flowability and enhance the quick-dissolve aspects of the co-processed carbohydrate system (compare FIG. 3 and FIG. 8).

The present invention also includes a composition which is not a quick-dissolve, may be produced by co-spray drying a polyol composition in an air stream, whereby the polyol composition is seeded with dry polyol particles. The resulting composition includes particles having a nonfilamentous microstructure.

Dry particles may be introduced at a rate of from about 1 kg/hr to about 100 kg/hr. Preferably, the feed rate is about 12.5 kg/hr to about 75 kg/hr, and more preferably, the feed rate is about 50 kg/hr More preferably, the dry feed rate is about 20 kg/hr. The feed rates apparently do not impact the morphology of the resulting product.

By way of example and not by limitation, a mannitol/sorbitol solution may be prepared having a total mass of 511 kg, 230 kg of which is attributed to the mannitol and sorbitol. At a total feed rate of about 75 kg/hr, about 20 kg/hr of dry particles will be introduced and about 55 kg/hr of the mannitol/sorbitol solution will be introduced into the spray dryer.

In another embodiment of the present invention, the solid preparation of the present invention comprises:
65-92% by weight of a polyol or mixture of polyols;
2-8% by weight of a cross-linked polyvinylpyrrolidone;
2-6% by weight of sodium croscarmellose use;
3-12% by weight of starch;
0.05-0.5% by weight silica gel; and
0.05-0.5% by weight colloidal silica.

In addition to the components identified above, the preparation may optionally contain from 8-28% by weight of other components that are suitable for ingestion by humans and which do not adversely affect the ability of the final solid preparation to completely dissolve or disperse within 60 seconds of being placed in the buccal cavity of the user.

In another embodiment of the present invention, the formulation comprises:
75-90% by weight of a polyol or mixture of polyols;
3-7% by weight of a cross-linked polyvinyl pyrrolidone;
1-4% by weight of sodium croscarmellose;
4-10% by weight of starch
0.05-0.3% by weight silica gel; and
0.05-0.3% by weight colloidal silica.

In another embodiment of the present invention, the formulation comprises:
80-88% by weight of a polyol or mixture of polyols;
3.5-6% by weight of a cross-linked polyvinyl pyrrolidone;
2.5-3.5% by weight of sodium croscarmellose;
5-9% by weight of starch;
0.05-0.25% by weight silica gel; and
0.05-0.25% by weight of colloidal silica.

In another embodiment of the present invention, the formulation comprises:
84-85% by weight of a polyol or mixture of polyols;
4-5% by weight of a cross-linked polyvinyl pyrrolidone;
2.9-3.2% by weight of sodium croscarmellose;
7-8% by weight of starch;
0.15-0.20% by weight silica gel; and
0.15-0.20% by weight of colloidal silica.

The polyols that are suitable for use in the formulation of the present invention are sorbitol, mannitol, maltitol, erythritol, xylitol and lactitol and mixtures of these polyols. In one embodiment of the present invention, the polyol or mixture of polyols used in the formulation includes at least one polyol selected from the group consisting of mannitol, maltitol and sorbitol.

In another embodiment of the present invention, the polyol component of the composition comprises spray-dried mannitol or a spray-dried mixture of mannitol and sorbitol or a spray-dried mixture of mannitol and xylitol.

In another embodiment of the present invention, two or more polyols or a polyol and a sugar (e.g., maltose) are coprocessed (e.g., by spray-drying or granulation techniques) to form the polyol component.

The compositions of the present invention provide the formulator with a flexible platform that can be used to prepare a variety of solid preparations that contain one or more active ingredients and will dissolve quickly in the buccal cavity of the user.

Many different disintegrating agents can be used to prepare the co-processed carbohydrate system. Such agents include, but are not limited to crospovidone, sodium croscarmellose, sodium starch glycolate, and mixtures thereof. The disintegrating agent is preferably present in the co-processed carbohydrate system in a range of from about 1 percent to about 20 percent of the total weight of the system. In one embodiment of the present invention, the disintegrating agent used to prepare the co-processed carbohydrate system is cross-linked polyvinyl pyrrolidone (crospovidone) and is present in the co-processed carbohydrate system at about 10 percent of the total weight of the system.

The cross-linked polyvinyl pyrrolidone, sodium croscarmellose and starch act to hasten the disintegration of the solid preparation by absorbing water.

Glidants useful in preparing the co-processed carbohydrate system include, but are not limited to silica gel, colloidal silica, precipitated silica, and mixtures thereof. The glidant component of the co-processed carbohydrate system preferably is present in a range of from about zero percent to about five percent of the total weight of the system. One embodiment of the present invention utilizes silica gel as the glidant in preparing the co-processed carbohydrate system, and the silica gel preferably is present in about 0.25 percent of the total weight of the system.

Preferred starches for use in the compositions of the present invention include pregelatinized starch, such as Starch 1500 (from Colorcon, West Point, Pa.) and National 1551 (National Starch & Chemical Co., Bridgewater, N.J.).

The silica gel acts to improve the flow properties of the composition and minimize the amount of material that sticks to the punches and dies during tableting. The colloidal silica acts to improve the flow properties of the composition before it is tableted.

In addition to the carbohydrate(s), disintegrating agent, and glidant (i.e., the co-processed carbohydrate system), the tablet composition may also comprise any of the following ingredients without affecting the quick-dissolve characteristic of the co-processed carbohydrate system:

One or more coated and/or uncoated active ingredients (AIs).
One or more flavors
One or more colors
One or more lubricants, including, but not limited to sodium stearyl fumarate, glyceryl behenate, and magnesium stearate ("flow aids")
Citric acid and/or ascorbic acid
One or more sweetening agents including, but not limited to sucralose, aspartame, and acesulfam-K
Tableting aids.

There is no limitation to the active ingredient (AI) that can be used with the present invention. Active ingredients include, but are not limited to pharmaceutical ingredients and nutraceutical ingredients. Examples of pharmaceutical ingredients that can be used include, but are not limited to gastrointestinal function conditioning agents, including, but not limited to bromopride, metoclopramide, cisapride, and domperidone; anti-inflammatory agents, including, but not limited to aceclofenac, diclofenac, flubiprofen, sulindac, and celecoxib; analgesics, including, but not limited to acetominophen and aspirin; agents for erectile dysfunction therapy, including, but not limited to sildenafil and apomorphine; anti-migraines, including, but not limited to sumatriptan and ergotamin; antihistaminic agents, including, but not limited to loratadine, fexofenadine, pseudoephedrine and cetirizine; cardiovascular agents, including, but not limited to nitroglycerine and isosorbide dinitrate; diuretics, including, but not limited to furocemide and spironolactone; anti-hypertensive agents, including, but not limited to propranolol, amlodipine, felodipine, nifedipine, captoprile, ramiprile, atenolol, and diltiazem; anti-hypolipidemic agents, including, but not limited to simvistatin, atrovastatin, and pravastatin; anti-ulcer agents, including, but not limited to cimietidine, ranitidine, famotidine, omeprazole, and lansoprazol; anti-emetics, including, but not limited to meclizine hydrochoride, ondansetron, granisetron, ramosetron, and tropisetron; anti-asthmatic agents, including, but not limited to aminophylline, theophylline, terbuttaline, fenoterol, formoterol, and ketotifen; anti-depressants, including, but not limited to fluoxetine and sertraline; vitamins, including, but not limited to B1, B2, B6, B12 and C; anti-thrombotic agents, including, but not limited to sulfinpyrazone, dipyridamole, and ticlopidine; chemotherapeutic agents, including, but not limited to cefaclor, bacampicillin, sulfamethoxazole, and rifampicin; hormones, including, but not limited to dexamethasone and methyltestosterone; anti-thelmintic agents, including, but not limited to piperazine, ivermectine, and mebendazole; and anti-diabetic agents, including, but not limited to acarbose, gliclazid, and glipizid.

Preferable pharmaceutical ingredients which may be used in the present invention include, but are non limited to acetaminophen, pseudoephedrine hydrochloride, dextromethorphan hydrobromide, dompereidone, famotidine, meclizine hydrochloride, scopolamine hydrobromide, ondansetron, cisapride, granisetron, sildenafil, loratadine, and amlodipine.

Examples of nutraceutical ingredients include, but are not limited to any ingredient that is thought to have a beneficial effect on human health. Such ingredients include coenzyme Q-10, chondroitoin, *echinacea*, ephedra, glucosamine, garlic, ginkgo *biloba, ginseng*, grape seed extract, guarana, hawthorn, herbs, kava, kola nut, lutein, St. John's wort, vinpocetine, and yohimbe.

There is no limitation on color or flavor that is useful in the present invention, and these characteristics will likely be chosen based on the age of the patient consuming the solid dosage form. Those of skill in the art will know which colors and flavors are useful in the present invention. Color and flavor are inert ingredients and generally do not have any effect on the efficacy of the tablet.

In one embodiment of the present invention, the co-processed carbohydrate formulation is directly compressed into a solid dosage form (e.g., a tablet) using a standard compression equipment (e.g., a tableting press). One embodiment of the directly compressed solid dosage form of the present invention interacts with saliva in the oral cavity of a patient and completely dissolves or disintegrates in the oral cavity into an easily swallowable form, preferably within about 60 seconds.

In an embodiment of the invention, the solid dosage form completely dissolves or disintegrates into an easily swallowable form within about 25 to 50 seconds after placing the tablet in the oral cavity.

The tablets produced in the present invention preferably have a tablet hardness in the range of about 10 newtons to about 100 newtons and a friability (standard USP test method) in the range of about 0.0 percent to about 5 percent.

In one embodiment of the present invention, the tablets produced have a tablet hardness in the range of about 20 newtons to about 60 newtons and a friability (standard USP test method) in the range of about 0.0 percent to about 2 percent, and would dissolve or disintegrate in the oral cavity within about 45 seconds.

Thus, preferably, the present invention makes it possible to produce high quality, robust tablets that show rapid dissolution or disintegration properties in a cost effective manner. The cost savings are primarily due to the inexpensive ingredients and processes involved, as described herein.

The quick dissolving formulations of the present invention may be used as a delivery platform for one or more active ingredients. One or more active ingredients may be mixed with the quick dissolving co-processed carbohydrate system and formed into a solid preparation, such as a tablet.

In another embodiment, additional ingredients such as a lubricant, flavor, color, or sweetening agent may also be added to the formulation and formed into a solid preparation.

When the solid preparation is placed in the oral cavity of a patient, it interacts with saliva and rapidly dissolves or disperses in the oral cavity of the patient. As the solid preparation dissolves in the oral cavity of the patient, it releases the one or more active ingredients contained in the solid preparation.

The following examples are given to illustrate the present invention. It should be understood, however, that the invention is not to be limited to the specific conditions or details described in these examples. Throughout the specification, any and all references to a publicly available document, including but not limited to a U.S. patent, are specifically incorporated by reference.

Example 1

Formulation A

A rapidly dissolving tablet in accordance with the present invention, was produced as follows. A mixture of 547.48 grams of co-processed carbohydrate system consisting of mannitol and sorbitol in a 90:10 ratio (SPI Pharma Inc., New Castle, Del.), 61.00 grams of Polyplasdone-XL (ISP Technologies, Wayne, N.J.) and 1.53 grams of Syloid®244 FP (W. R. Grace & Co., Columbia, Md.) were blended in a Turbula Mixer for 10 minutes.

Formulation A (600.6 grams) was then blended in an 8-quart V-blender along with 113.48 grams of acetaminophen microcaps, 16.64 grams of pseudoephedrine HCl microcaps and 25.664 grams of dextromethorphan HBr microcaps (Eurand America Inc., Vandalia, Ohio), 16 grams of Grape Flavor # FAEB895 (Wild Flavors, Inc., Cincinnati, Ohio), 2 grams of sucralose (Ortho-McNeil Pharmaceuticals Raritan, N.J.), 8 grams of anhydrous citric acid, and purple color # LB1868 (Colorcon, West Point, Pa.) for 10 minutes. Sixteen grams of sodium stearyl fumarate (Penwest Pharma, Patterson, N.Y.) was added to the mixture and the mixture was blended for 6 minutes. The blend was then discharged and tableted using standard tableting procedures.

Example 2

Formulation B

A rapidly dissolving tablet was produced as follows. A mixture of 547.48 grams of spray-dried mannitol (about 80% of total formulation) blended with granular sorbitol (about 10% of total formulation), 61.00 grams of Polyplasdone-XL (ISP Technologies, Wayne, N.J.) and 1.53 grams of Syloid®244 FP (W. R. Grace & Co., Columbia, Md.) were dry-blended in a Turbula Mixer for 10 minutes.

Formulation B (600.6 grams) was then blended in an 8-quart V-blender along with 113.48 grams of acetaminophen microcaps, 16.64 grams of pseudoephedrine HCl microcaps and 25.664 grams of dextromethorphan HBr microcaps (Eurand America Inc., Vandalia, Ohio), 16 grams of Grape Flavor # FAEB895 (Wild Flavors, Inc., Cincinnati, Ohio), 2 grams of sucralose (Ortho-McNeil Pharmaceuticals Raritan, N.J.), 8 grams of anhydrous citric acid, and purple color # LB1868 (Colorcon, West Point, Pa.) for 10 minutes. Sixteen grams of sodium stearyl fumarate (Penwest Pharma, Patterson, N.Y.) was added to the mixture and the mixture was blended for 6 minutes. The blend was then discharged and tableted using standard tableting procedures.

Example 3

Formulation C

A rapidly dissolving tablet was produced as follows. A mixture of 547.48 grams of spray-dried mannitol (about 80% of total formulation) blended with spray-dried sorbitol (about 10% of total formulation; SPI Pharma Inc., New Castle, Del.), 61.00 grams of Polyplasdone-XL (ISP Technologies, Wayne, N.J.) and 1.53 grams of Syloid®244 FP (W. R. Grace & Co., Columbia, Md.) were dry-blended in a Turbula Mixer for 10 minutes.

Formulation C (600.6 grams) was then blended in an 8-quart V-blender along with 113.48 grams of acetaminophen microcaps, 16.64 grams of pseudoephedrine HCl microcaps and 25.664 grams of dextromethorphan HBr microcaps (Eurand America Inc., Vandalia, Ohio), 16 grams of Grape Flavor # FAEB895 (Wild Flavors, Inc., Cincinnati, Ohio), 2 grams of sucralose (Ortho-McNeil Pharmaceuticals Raritan, N.J.), 8 grams of anhydrous citric acid, and purple color # LB1868 (Colorcon, West Point, Pa.) for 10 minutes. Sixteen grams of sodium stearyl fumarate (Penwest Pharma, Patterson, N.Y.) was added to the mixture and the mixture was blended for 6 minutes. The blend was then discharged and tableted using standard tableting procedures.

Example 4

Formulation D

A rapidly dissolving tablet in accordance with the present invention, was produced as follows. A mixture of 547.48 grams of co-processed carbohydrate system consisting of mannitol and sorbitol in an 80:20 ratio (SPI Pharma Inc., New Castle, Del.), 61.00 grams of Polyplasdone-XL (ISP Technologies, Wayne, N.J.) and 1.53 grams of Syloid®244 FP (W. R. Grace & Co., Columbia, Md.) were blended in a Turbula Mixer for 10 minutes.

Formulation D (600.6 grams) was then blended in an 8-quart V-blender along with 113.48 grams of acetaminophen microcaps, 16.64 grams of pseudoephedrine HCl microcaps and 25.664 grams of dextromethorphan HBr microcaps (Eurand America Inc., Vandalia, Ohio), 16 grams of Grape Flavor # FAEB895 (Wild Flavors, Inc., Cincinnati, Ohio), 2 grams of sucralose (Ortho-McNeil Pharmaceuticals Raritan, N.J.), 8 grams of anhydrous citric acid, and purple color # LB1868 (Colorcon, West Point, Pa.) for 10 minutes. Sixteen grams of sodium stearyl fumarate (Penwest Pharma, Patterson, N.Y.) was added to the mixture and the mixture was blended for 6 minutes. The blend was then discharged and tableted using standard tableting procedures.

Table 1 represents the composition of a tablet of any of the formulations:

TABLE 1

Composition of a Tablet

| Ingredient | mg/Tablet |
| --- | --- |
| Formulation A, B, C or D | 900.9 |
| Coated Acetaminophen | 170.22 |
| Coated Pseudoephedrine HCl | 24.96 |
| Coated Dextromethorphan HBr | 38.496 |
| Flavor (grape) | 24 |

TABLE 1-continued

Composition of a Tablet

| Ingredient | mg/Tablet |
| --- | --- |
| Sweetener (sucralose) | 3 |
| Citric acid | 12 |
| Color (purple) | 2.4 |
| Lubricant (sodium stearyl fumarate) | 24 |

Compaction profiles, that is, determination of maximum tablet hardness values, friability values, and disintegration time for each of the Formulations A, B, C and D were determined.

Results

Compaction Profile of the Formulations

FIG. 1 shows that a 100 percent increase in tablet hardness is attained using the co-spray dried carbohydrate systems (Formulations A and D) compared to simple dry-blending of the ingredients (Formulations B and C). Formulation D achieved the highest tablet hardness at 11.5 KP, and capping was not observed.

At a compression force of 13 KN, Formulations A and D both display at least double the tablet hardness of either Formulation B or C. At a compression force of 15 KN, Formulation B caps at a tablet hardness value of 3.3, while Formulations A and D have tablet hardness values of about 6.2 and 7.9, respectively, almost double the tablet hardness of Formulation B. At a compression force of 17 KN, Formulation C caps at a tablet hardness of 3.85 KP, while Formulations A and D exhibit tablet hardness values of about 8 and 9.9, respectively. Thus, Formulations A and D exhibit a trend of averaging at least about double the tablet hardness of Formulations B and C at any given compression force.

Therefore, the co-spray dried carbohydrate system is superior as compared to simply dry-blended ingredients, in preparing tablets with at least a 100 percent increase in tablet hardness over dry-blended ingredients.

TABLE 2

Maximum Hardness Values

| Formulation | Maximum Attainable Hardness (KP) before Capping is observed |
| --- | --- |
| Formulation A | 9.2 ± 1.2 KP |
| Formulation B | 3.3 ± 0.3 KP |
| Formulation C | 3.9 ± 0.8 KP |
| Formulation D | 11.6 ± 0.5 KP (No capping observed) |

Friability of the Formulations

Figure 2:
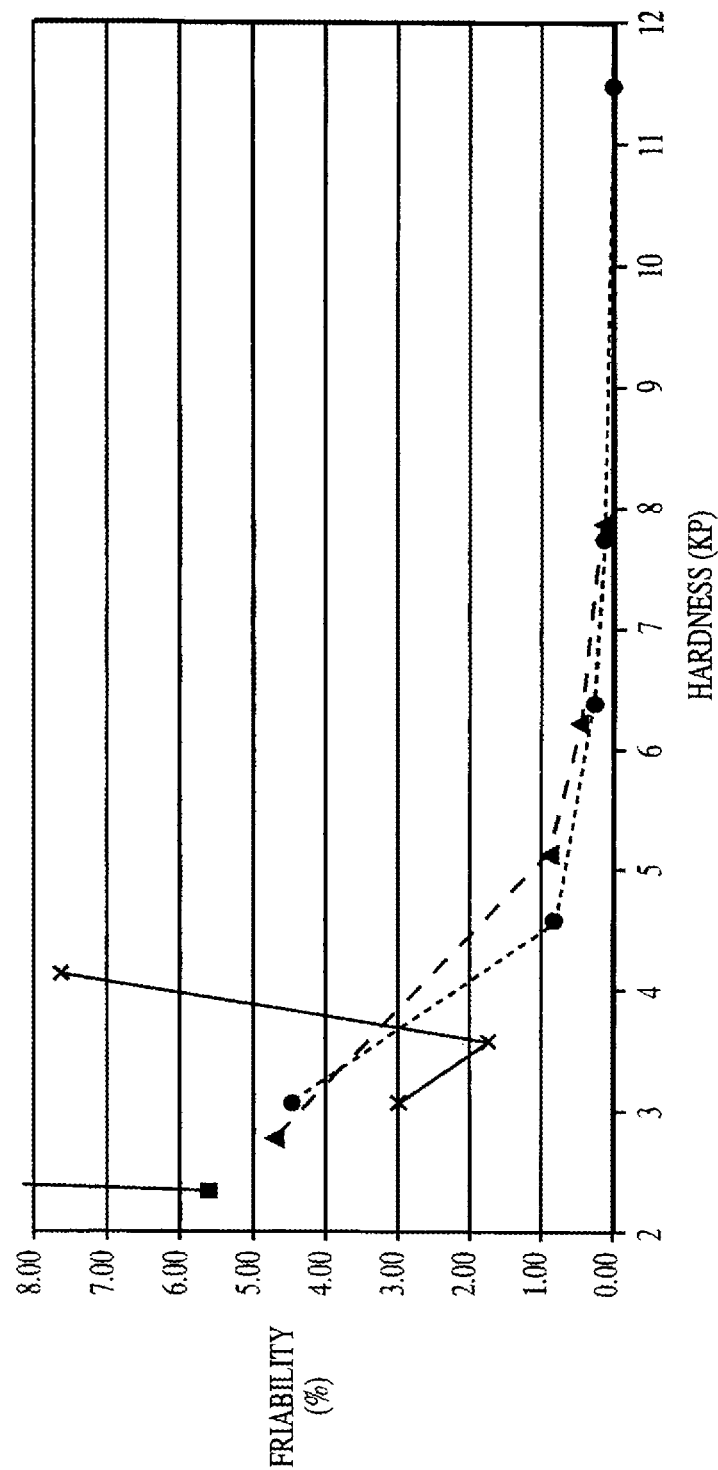
FIG. 2 is a graph depicting friability values versus tablet hardness for each of Formulation A (triangle), Formulation B (square), Formulation C ("x"), and Formulation D (circle).

A friability value of about 1 percent or less is desirable for tablets in order for them to withstand the stress of handling during production, packaging, and transport. Formulations A and D achieved low friability levels as shown in FIG. 2, which friability remained low, and even decreased as tablet hardness increased. For example, at a tablet hardness of about 4 KP, friability of Formulations A and D were about 1 percent, while friability for Formulation C was at about 7.5 percent. Formulation B, at a tablet hardness of about 2.5 KP, had a friability of 5.5 percent, and was subsequently eliminated. Only Formulations A and D had tablet hardness of greater than 4 KP, and friability decreased steadily to about 0.1 percent at a tablet hardness 8 KP. At 11 KP, only Formulation D remained, and friability was essentially zero.

The overall trend shown in FIG. 2 is that friability essentially decreases as tablet hardness increases. In order for a tablet to withstand stresses associated with handling and packaging, the need for tablets with increased hardness values (and therefore decreased friability values as FIG. 2 indicates) is required. Only Formulations A and D, which comprise the co-processed carbohydrate system, attain higher tablet hardness values thereby resulting in decreased friability values.

Thus, the co-spray dried carbohydrate system achieves a much lower friability percent as compared with the same ingredients prepared as dry-blends.

Disintegration Times in Oral Cavity for Different Formulations

Figure 3:
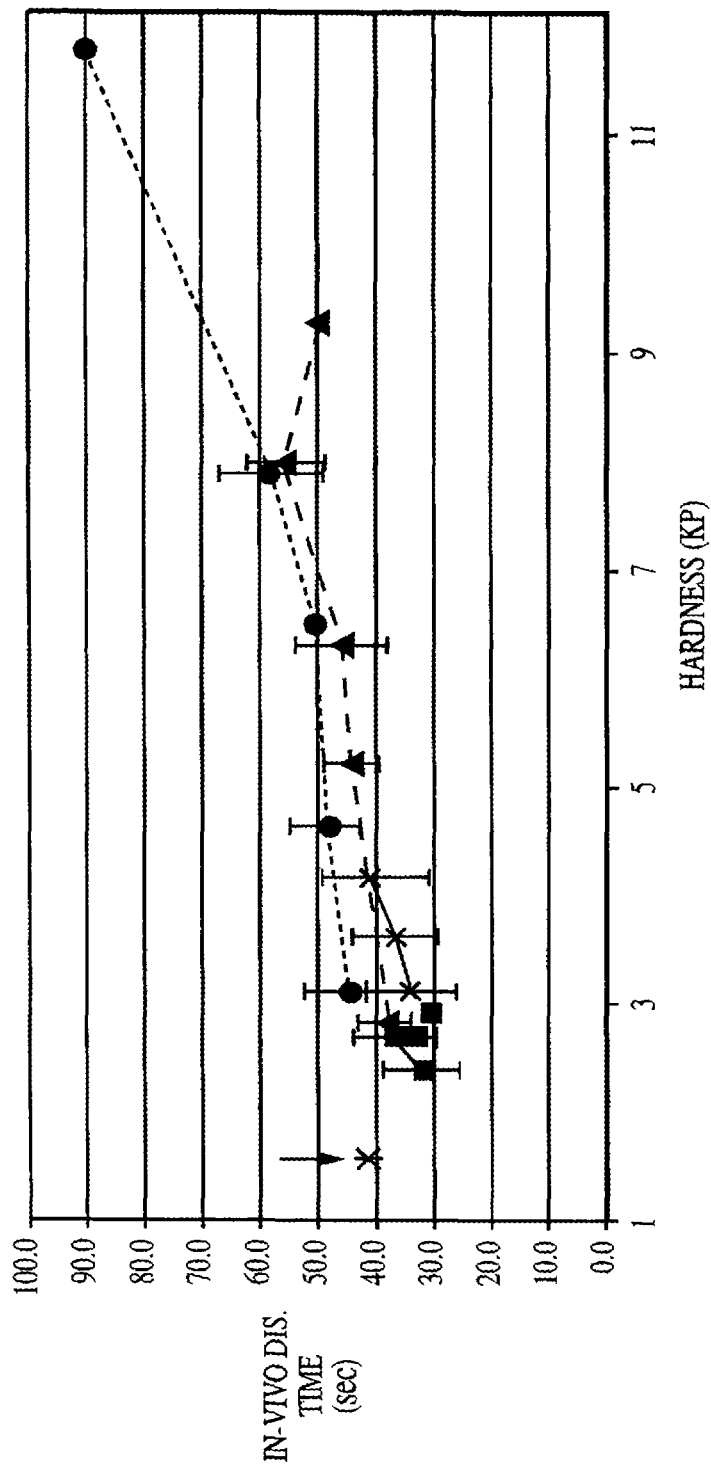
FIG. 3 is a graph depicting disintegration times versus tablet hardness for each of Formulation A (triangle), Formulation B (square), Formulation C ("x"), and Formulation D (circle). The large asterisk at about 1.5 KP represents an over-the-counter quick dissolve product.

FIG. 3 shows disintegration times in the oral cavity, for the Formulations A, B, C, and D. Disintegration time ranged from about 30 seconds to about 60 seconds varying with tablet hardness up to about 8 KP. Over-the-counter quick-dissolve tablets provide a reference point (indicated by an arrow), having a tablet hardness of about 1.5 KP and a disintegration time of about 42 seconds.

Formulation A tablet hardness ranged from about 2.5 KP to about 9.2 KP, and in-vivo disintegration times for Formulation A ranged from about 37 seconds to about 55 seconds, increasing steadily from a hardness of about 2.5 KP to about 8 KP. Disintegration time dropped off to about 49 seconds when measured at a tablet hardness of about 9.5 KP.

Formulation B had a tablet hardness range of about 2 to about 3 KP. Disintegration times for Formulation B ranged from about 30 to about 35 seconds, with no discernible relationship to tablet hardness.

Formulation C displayed a tablet hardness range of from about 3 to about 4 KP. Disintegration times for Formulation C increased steadily as tablet hardness increased, from about 32 seconds to about 40 seconds.

Formulation D exhibited a tablet hardness range of from about 3 KP to about 11.5 KP. From about 3 KP to about 8 KP, disintegration time increased steadily from about 42 seconds to about 58 seconds. From about 8 KP to about 11.5 KP, disintegration time increased more dramatically from about 58 seconds to about 90 seconds.

At a tablet hardness of about 3 KP, all of the formulations have a disintegration time of between about 30 and 45 seconds, however, the error bars shown within each of the Formulations indicate that variance within this range is not substantially significant. At a tablet hardness of about 4 KP, Formulations A, C, and D exhibited disintegration times of between about 40 and 45 seconds, also which variance is insignificant. Formulation B did not achieve a tablet hardness beyond about 3.3 KP.

At a tablet hardness of about 8, Formulations A and D exhibited disintegration times of about 55 and 58 seconds, respectively, and this difference, according to the standard error, is not significant.

Overall, disintegration times do not exceed 60 seconds over any tablet hardness up to about 9.2 KP. Disintegration time stayed fairly constant between tablet hardness values of about 4 KP and about 7 KP, and increased only slightly, by about 5 seconds between tablet hardness values of about 7 KP and 8 KP. Again, the error bars indicate that this slight increase in disintegration time is insignificant. Thus, it can be concluded that tablet hardness has no substantial effect on in vivo disintegration time (referring to disintegration time within the buccal cavity).

The co-spray dried carbohydrate system in Formulations A and D achieve lower friability and increased tablet hardness, but do not substantially affect the quick-dissolving disintegration properties of the tablet as compared with Formulations B and C.

The data from the above experiments clearly show that the co-spray dried carbohydrate system provides strong, high-quality tablets that are robust enough to withstand the stress of handling and transport while retaining rapid dissolution or disintegration properties.

Example 5

Preparation of a Mannitol:Sorbitol Co-Processed Carbohydrate

The main objective of this experiment was to compare the quality of agglomerates produced from spray drying a mixture of mannitol and sorbitol in the proportion of about 88% Mannitol to about 12% Sorbitol, using mannitols supplied by SPI Pharma, Inc. (New Castle, Del.), GETEC (Brazil), and Cerestar (France). The sorbitol was crystalline and was provided by SPI Pharma, Inc. (New Castle, Del.). Another objective was to maintain a low moisture content, preferably less than 1%.

Materials and Methods

The following materials were used to carry out the present experiment: GETEC Mannitol Batch No. 10519387 (Item No. 10133), SPI Pharma Batch No. 3086E2 (MANNO-GEM-EZ™ Powder Mannitol), Cerestar Batch No. GQ8641 (C* MANNIDEX™ 16700), and Sorbitol Batch No. 4071C2 (SORBOGEM™, SPI Pharma, Inc). A S1 Spray Fluid Bed Dryer, capable of operating at up to 450° C. inlet temperature was used to conduct the experiment.

The mannitol:sorbitol composition ("feed") was prepared in a steam jacketed tank with deionized water at 85° C. 220 kilograms of mannitol powder and 30 kilograms of sorbitol were dissolved in the hot water. The feed solids concentration was calculated to be between 45 and 46% using an Infra Red Moisture Analyser. A 7" CSE disc was used to atomize the feed. The inlet temperature was varied between 190 and 210° C. during the trials and the outlet temperature was varied, by adjusting the feed rate, to between 90 and 92° C.

Feed batch 1 was made up using MANNOGEM-EZ™. The initial operating parameters included a disc speed of 11,500 rpm, spray dryer outlet temperature of 89° C., and a fluid bed outlet temperature of 92° C. The product moisture of sample 1 was 1.03% with a particle size of 35% greater than 125 microns.

In Sample 2, a slightly higher fluid bed outlet temperature of 96° C. was used. This produced a product having a moisture content of 0.98%, with a particle size of 80.39% greater than 125 microns.

Spray dryer operating parameters were adjusted to operate with a dryer inlet air temperature of 205° C. and a dryer outlet air temperature of 92° C. for Sample 3. The fluid bed air temperature rose to 99° C. using these parameters. The product demonstrated a moisture content of 1.75%. The product particle size was assessed as 79.45% greater than 125 microns.

Sample 4 was assessed using alternative parameters. The spray dryer inlet temperature was adjusted to 210° C., with an outlet temperature of 95° C., and a fluid bed air temperature of 94° C. Sample 4 had a moisture of 1.35%, and a total of 81.98% of particles above 125 microns.

Finally, the dryer was adjusted to give an inlet air temperature of 190° C., outlet air temperature of 90° C., and a fluid bed air temperature of 94° C. Sample 5 showed a moisture level of 1.30%, with 52.31% of particles above 125 microns.

Five samples of Feed batch 2, prepared from C* MANNIDEX™ and SORBOGEM™ were tested using the same drying conditions as above. Product moisture results averaged 0.96%, and particle size averaged about 55.3% above 125 microns.

Feed batch 3 was prepared from GETEC mannitol and SORBOGEM™. Trials were carried out under the same set of plant operating parameters as those for batch one, and no adverse conditions were observed. The products recovered ranged in moisture content from 0.83% to 0.97%, with particle sizes between 48% and 61% greater than 125 microns.

Feed batch 4 was prepared from the same materials as Feed batch 1, and in addition, a method of dry mix addition into the fines recycle system of the dryer was employed ("seeding"). This was achieved using a vibratory feeder which was positioned at the inlet to the fines recycle fan. The dry feed used in the feeder was a dry blend of a 88:12 ratio of GETEC mannitol to SORBOGEM™. The mannitol and sorbitol powders were blended in a ribbon blender prior to loading the vibratory feeder. The reason for the use of GETEC mannitol for the dry addition was due to insufficient stock of MANNOGEM-EZ™ being available.

The main spray dryer feed was prepared using MANNO-GEM-EZ™ and SORBOGEM™. The feed rate for the dry addition vibratory feeder was set at 50 kilograms per hour in order to match the approximate wet feed rate of the spray dryer. Although each set of conditions was intended to be carried out in this experiment, only three of the four conditions were tested due to failure of the product discharge valve on the fluid bed. From the laboratory analysis of the samples produced, it would appear that the addition of dry material into the fines recycle system results in the production of an overall drier product. Moistures in the product of 0.3-0.6% were recorded, and product particle sizes were slightly finer than those observed during the previous trials.

Dry solids addition into the fines recycle system appears to be beneficial to achieving lower residual product moistures.

Figure 5A:
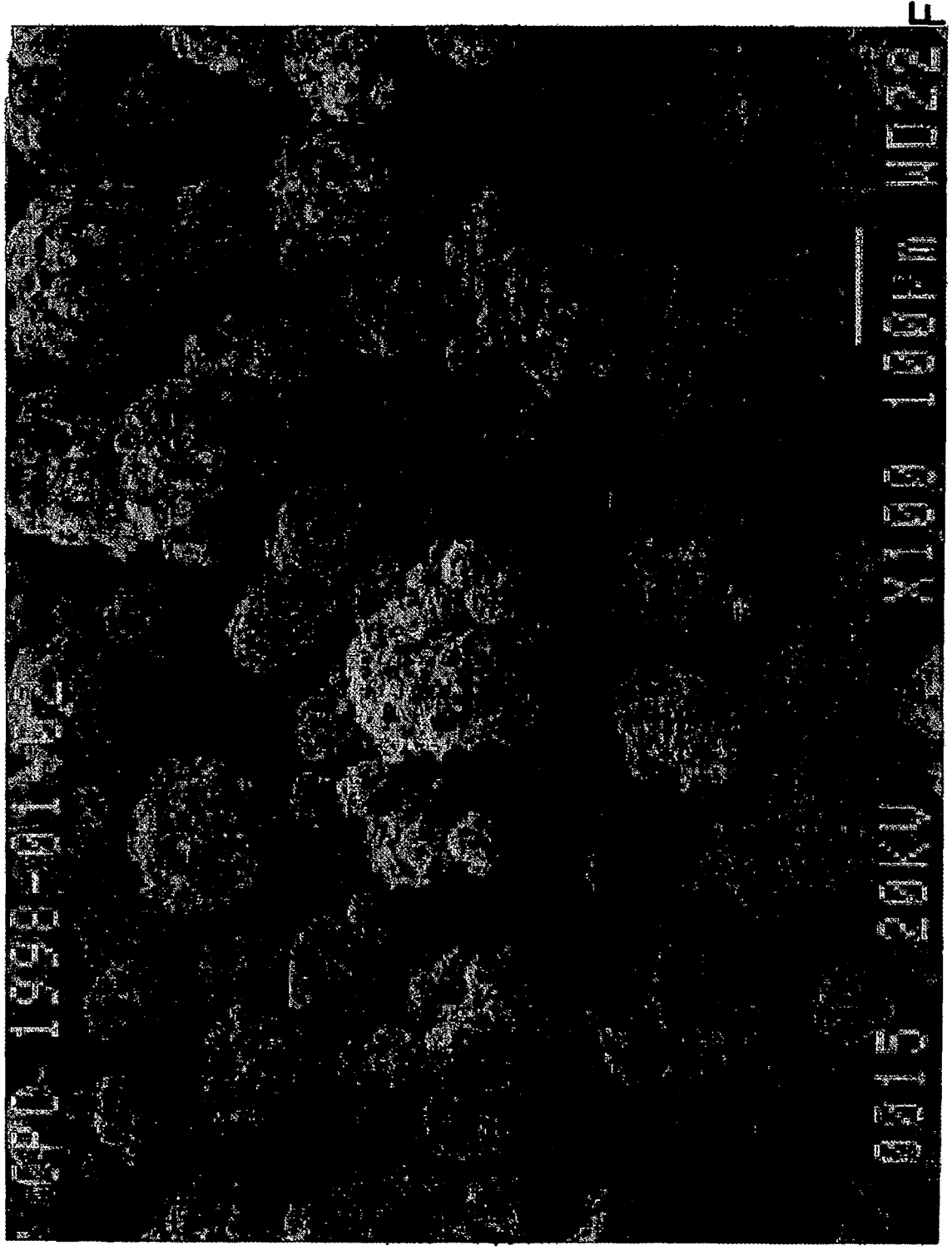
FIGS. 5A-5H include a set of scanning electron micrographs (SEMs) of different commercially available mannitol compositions after they are dried in the spray dryer.
Figure 5B:
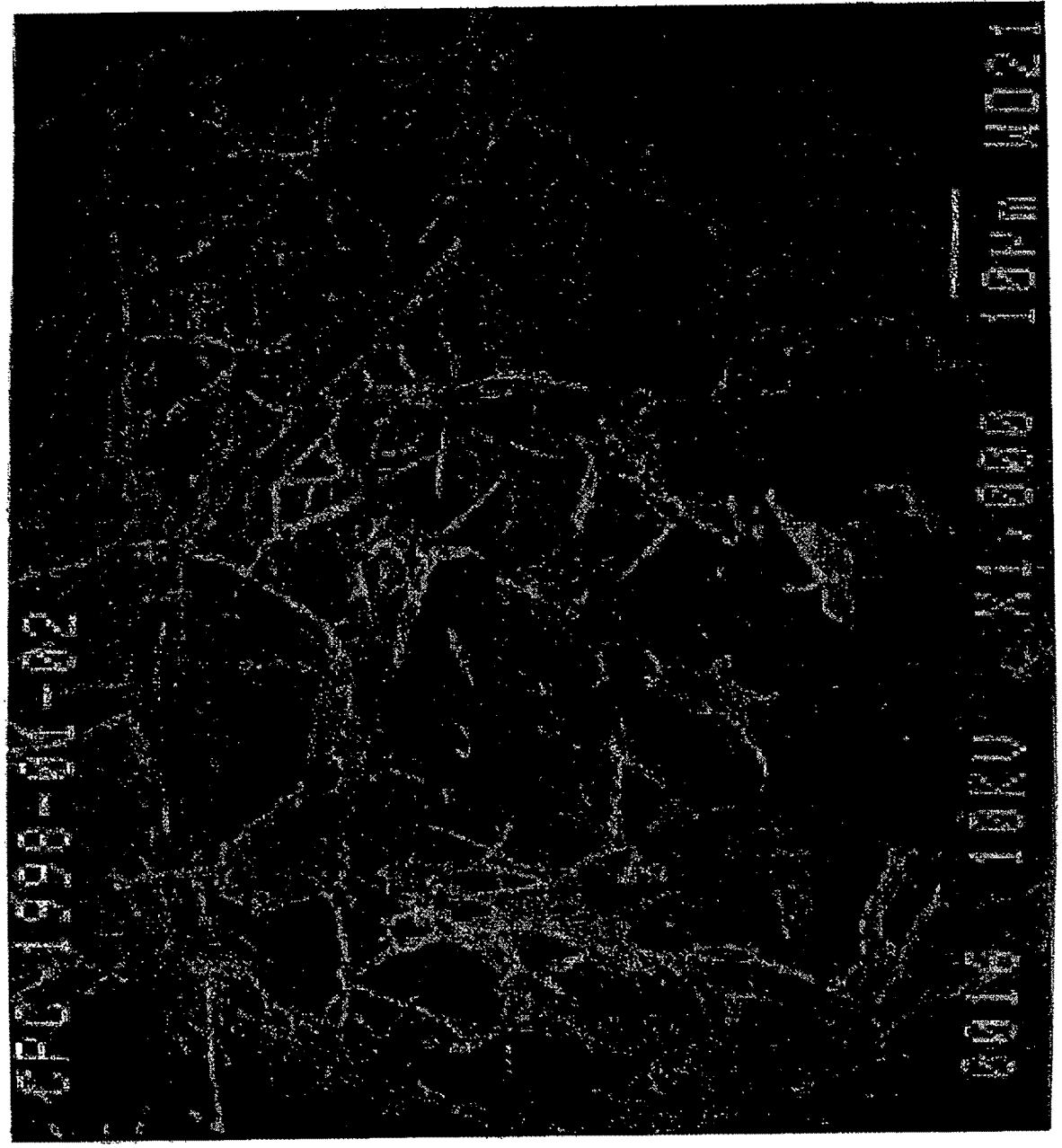
Figure 5C:
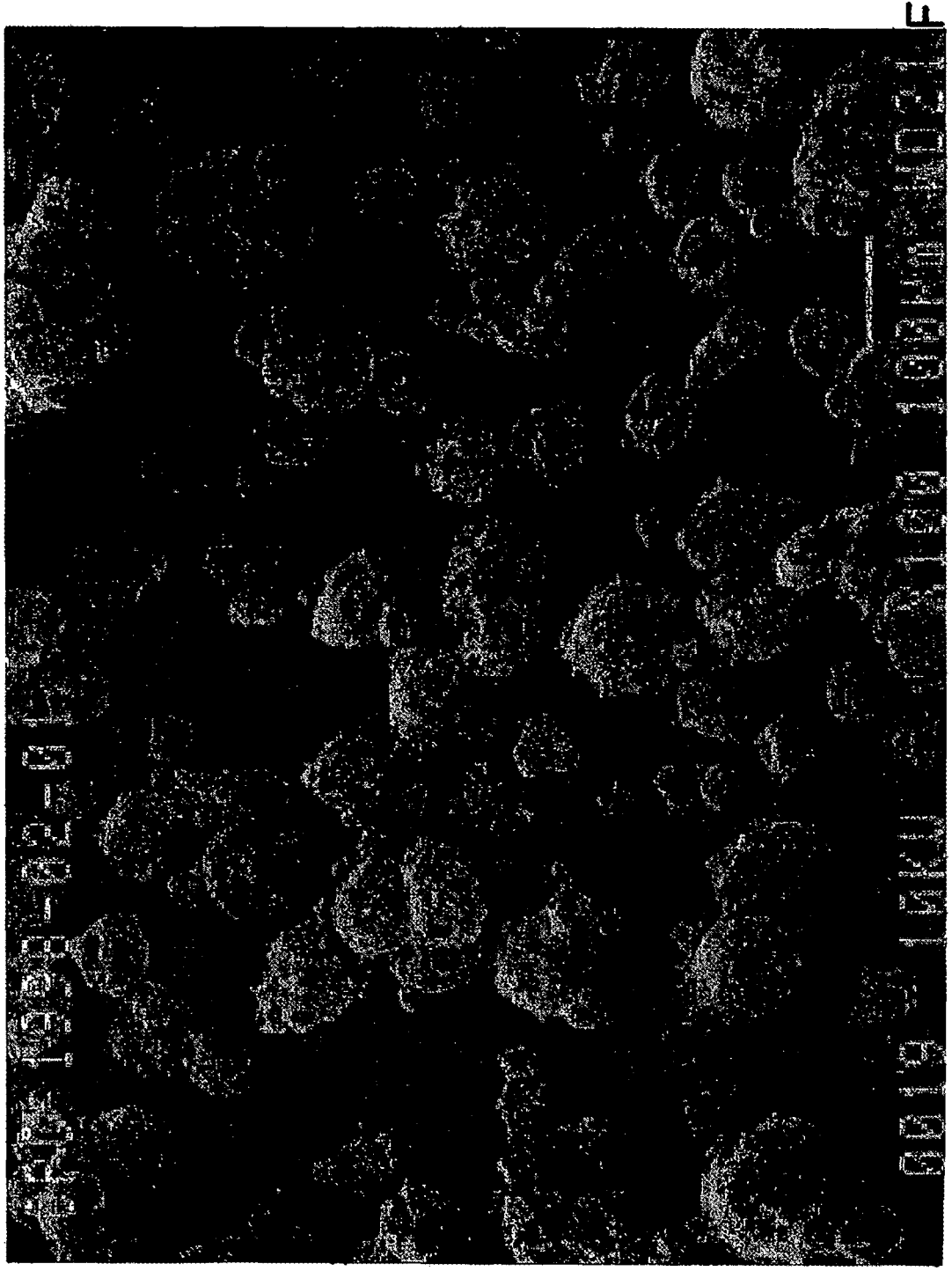
Figure 5D:
Figure 5E:
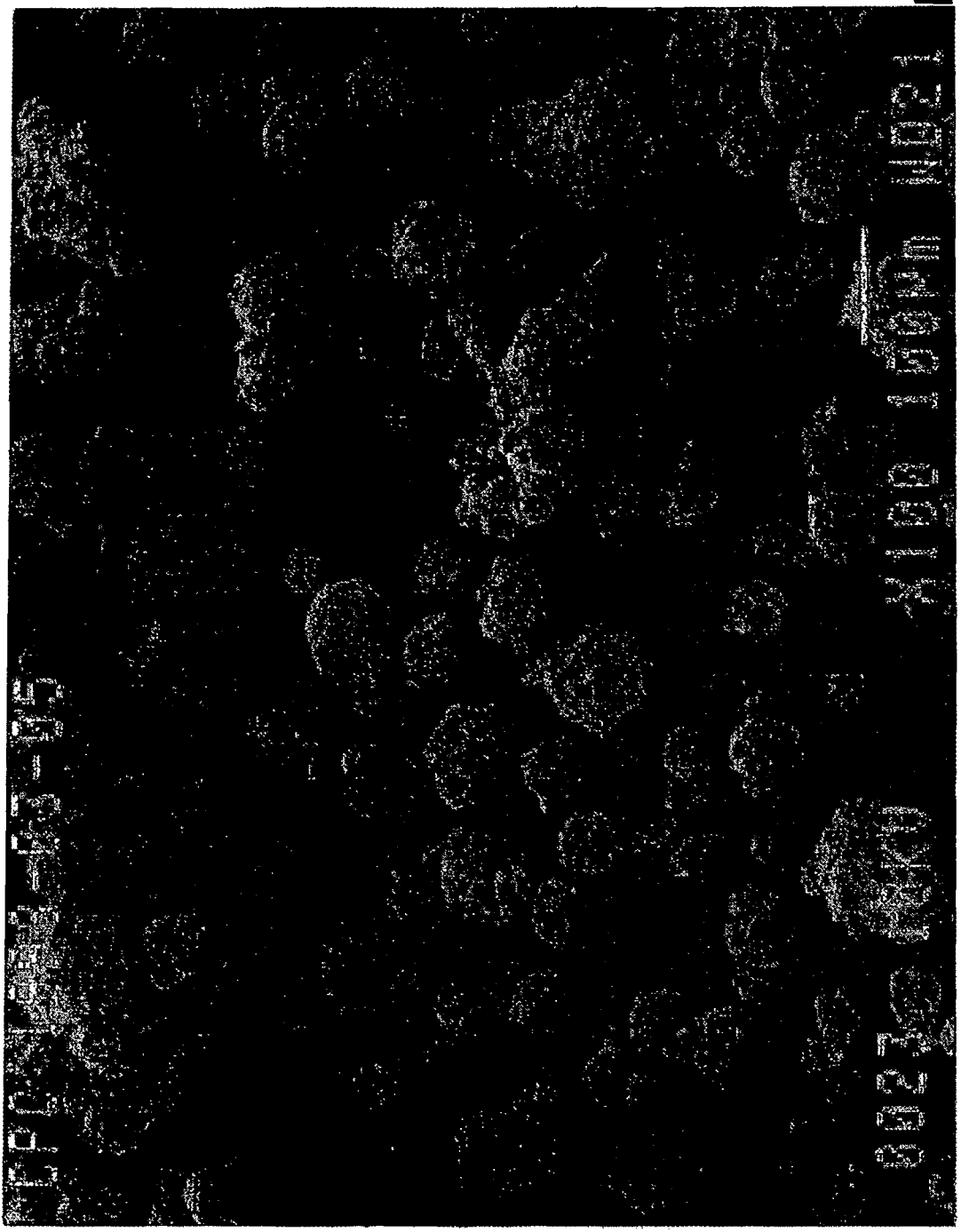
Figure 5F:
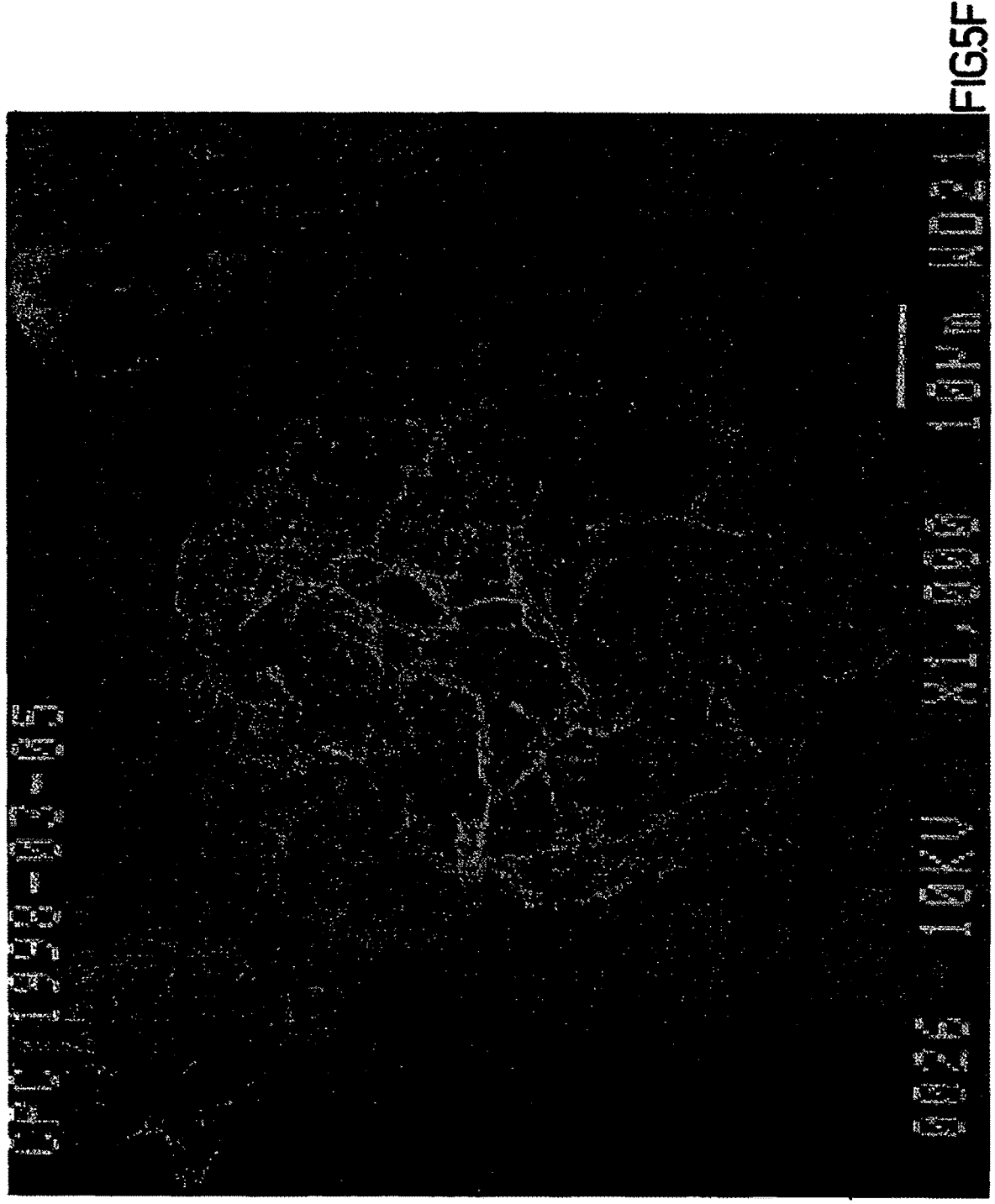
Figure 5G:
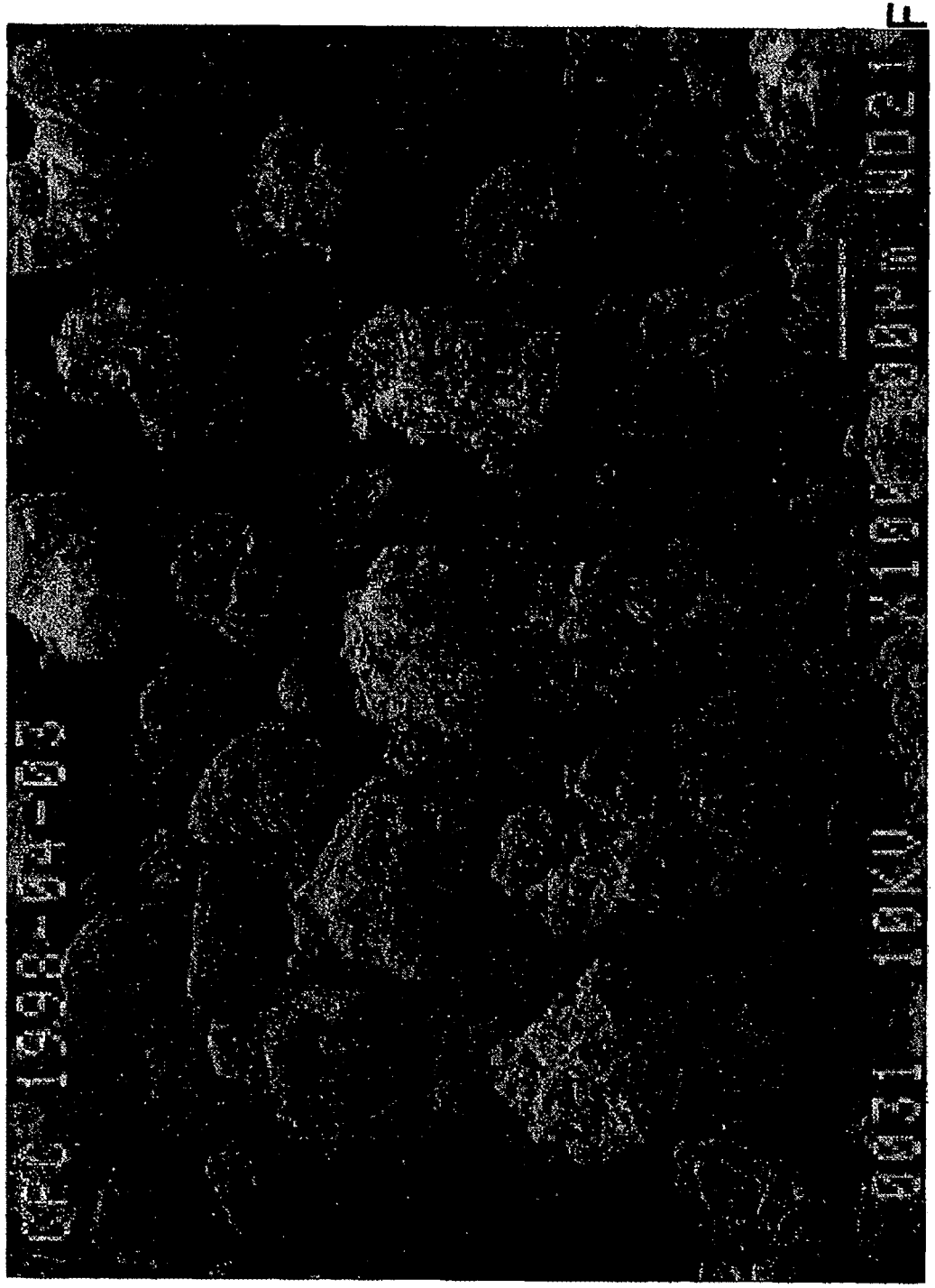
Figure 5H:
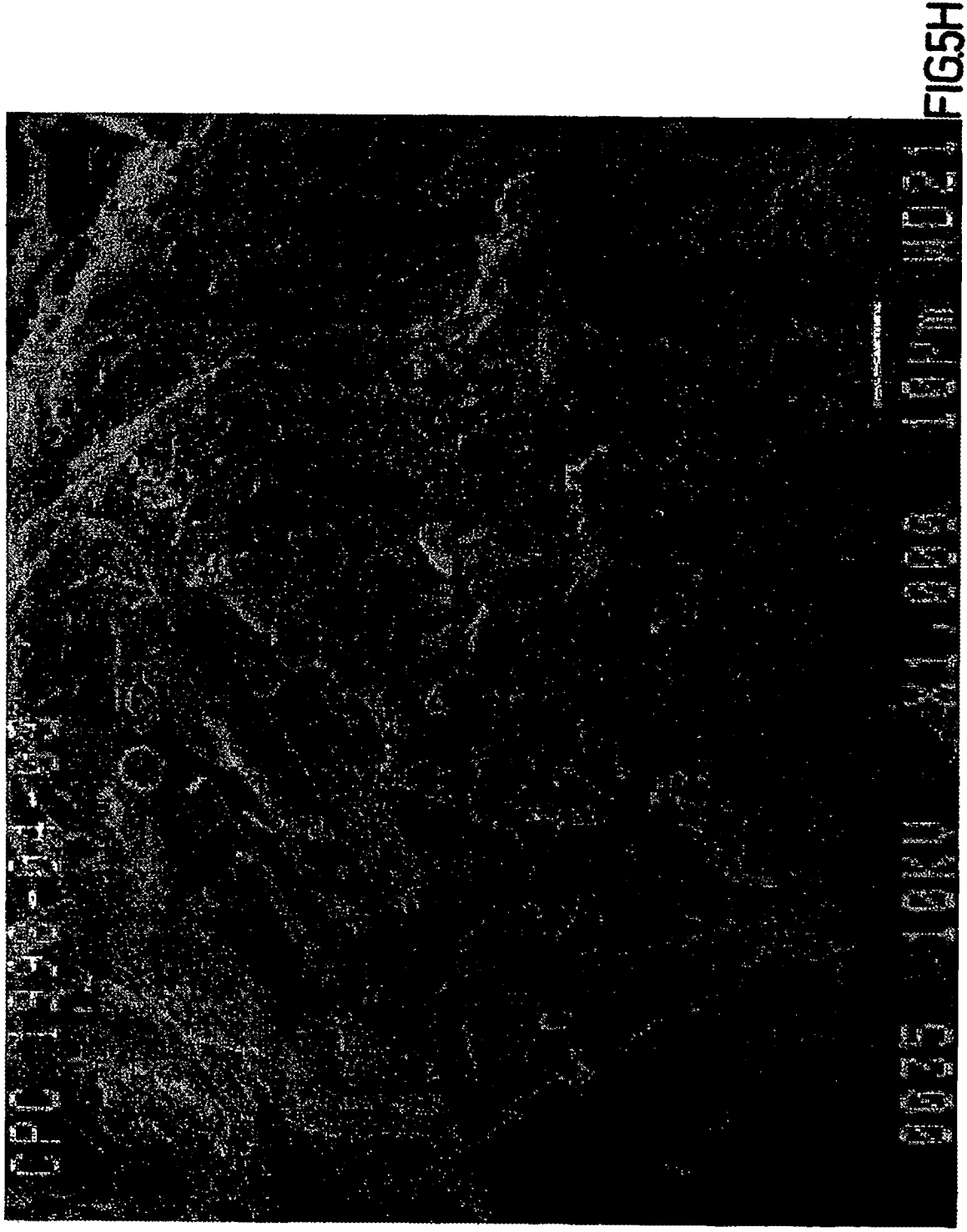

FIGS. 5A-5H illustrate the spherical nature of each of the spray-dried final products containing an 88:12 ratio of co-spray dried mannitol:sorbitol as demonstrated by scanning electron microscopy. FIG. 5A is a SEM showing the co-processed particle resulting from use of the MANNO-GEM-EZ™ in the co-spray drying process without seeding. FIG. 5B is a 100× magnification of FIG. 5A and shows a spherical structure having a somewhat filamentous structure on its surface. The moisture content for this particle was determined to be 1.0%.

FIG. 5C is a SEM showing the co-processed particle resulting from use of the C* MANNIDEX™ in the co-spray drying process without seeding. FIG. 5D is a 100× magnification of FIG. 5C and shows a spherical structure having a somewhat filamentous structure on its surface. The moisture content for this particle was determined to be 0.96%.

FIG. 5E is a SEM showing the co-processed particle resulting from use of the GETEC mannitol in the co-spray drying process without seeding. FIG. 5F is a 100× magnification of FIG. 5E and shows a spherical structure having a somewhat filamentous structure on its surface. The moisture content for this particle was determined to be 0.82%.

FIG. 5G is a SEM showing the co-processed particle resulting from use of the MANNOGEM-EZ™ in the co-spray drying process with seeding. FIG. 5H is a 100× magnification of FIG. 5G and shows a spherical structure which is non-filamentous on its surface. The moisture content for this particle was determined to be 0.3%. It is thought that the addition of the seeding step significantly decreased the moisture content of the resulting co-processed particle. Further, with seeding, little or no filamentous morphology is exhibited on the surface of the resulting particle. As discussed above, lack of filamentous structure on the surface of the resulting co-spray dried particle may lead to increased flowability and enhanced quick-dissolve properties.

Table 3, below, illustrates representative values for the results of the experiments detailed above.

TABLE 3

| | | Batch No. | | |
|---|---|---|---|---|
| | 1 | 2 | 3 | 4 |
| Sample No. | 2 | 1 | 5 | 3 |
| Disc Type (CSE) | 7" | 7" | 7" | 7" |
| Disc Speed (RPM) | 11500 | 11500 | 13000 | 13000 |
| Inlet Temp. (° C.) | 199 | 192 | 210 | 189 |
| Outlet Temp. (° C.) | 90 | 87 | 93 | 91 |
| Fluid Bed Inlet Temperature (° C.) | 116 | 118 | 115 | 115 |
| Fluid Bed Outlet Temperature (° C.) | 96 | 98 | 95 | 94 |
| Total Run Time (mins) | 30 | 55 | 80 | 38 |
| Prod. Weight (kg) | 33.1 | 30 | — | 33.78 |
| *Prod. Moisture (%) | 0.98 | 0.96 | 0.83 | 0.33 |
| +Particle Size Cum. >250µ (%) | 2.2 | 1.2 | 1.4 | 7.9 |
| >200µ (%) | 9.6 | 4.9 | 2.6 | 15.9 |
| >125µ (%) | 80.4 | 49.2 | 47.9 | 44.9 |
| >100µ (%) | 96.9 | 87.3 | 90.0 | 78.0 |
| >90µ (%) | 99.6 | 98.7 | 98.21 | 91.0 |
| <90µ (%) | 100 | 100 | 100 | 100 |

*Product Moisture measured by Karl Fisher AF8.
+Particle size measured with 200 mm sieves using the soft brush method after being on a sieve shaker.

Example 6

Differences in Morphology and Quick-Dissolve Aspects Based on Feed Rate of Dry Blend During Seeding Experiments were performed as described above in Example 5 for "Batch 4". Various dry feed rates for seeding were tested to determine whether the dry feed rate had an impact on morphology of the resulting particle. Feed rates of about 12.5 kg/hr, 50 kg/hr, and 75 kg/hr were tested on placebo formulations of co-spray dried 88:12 mannitol:sorbitol mixtures, which were seeded with a dry blend of an 88:12 mannitol:sorbitol mixture. A co-granulated blend of co-spray dried mannitol (MANNOGEM EZ™, SPI Pharma, Inc.) and crystalline sorbitol (SORBOGEM™, SPI Pharma, Inc.) in a ratio of 88:12 was run as a control.

Figure 7:
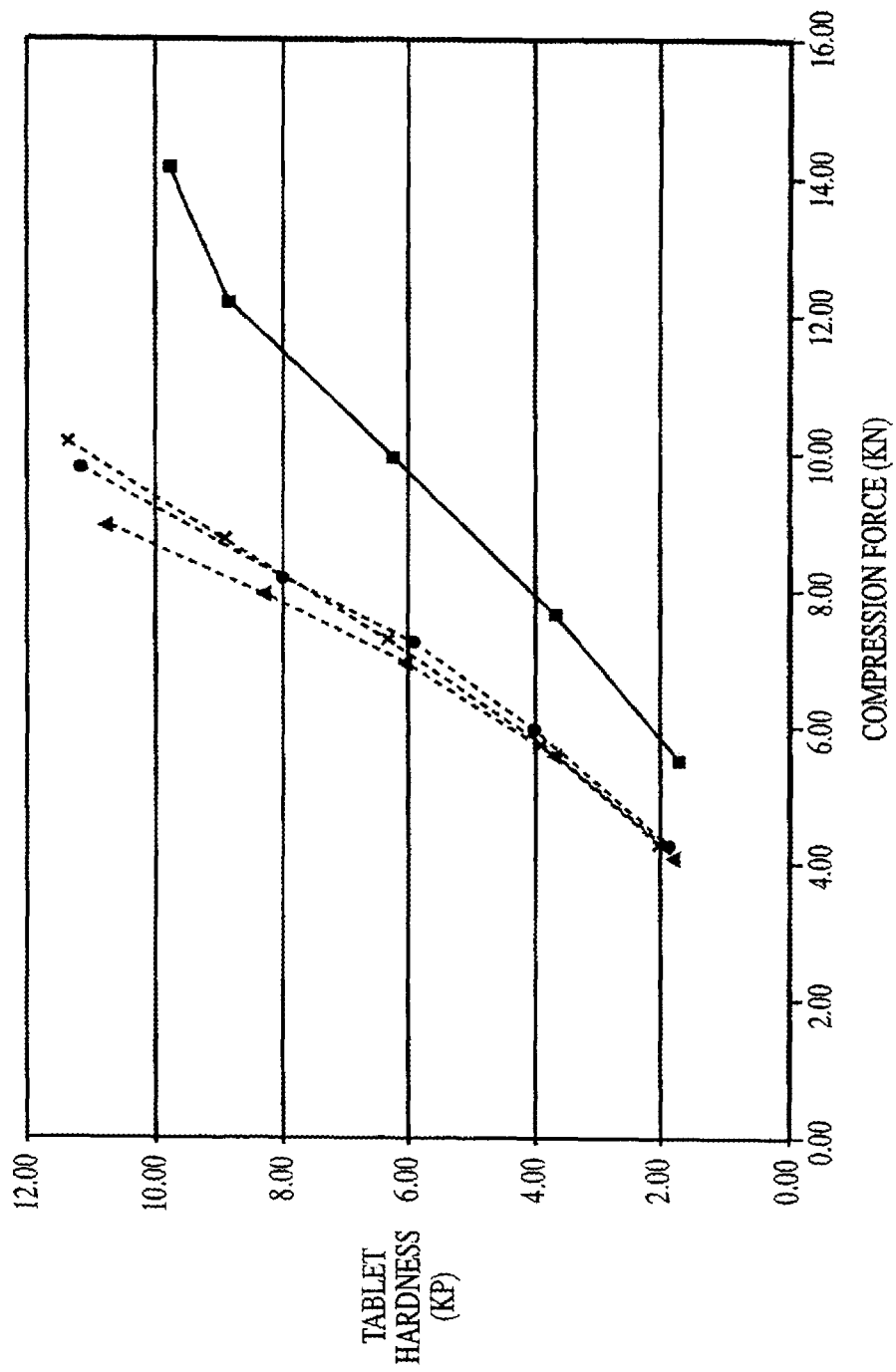
FIG. 7 is a graph illustrating the compactibility of a placebo formulation of co-spray dried mannitol:sorbitol mixtures seeded with dry blends of mannitol:sorbitol in the same ratio at varying feed rates. Data is represented as follows: co-spray dried mannitol:sorbitol placebo having a feed rate of 12.5 kg/hr (circle); co-spray dried mannitol:sorbitol placebo having a feed rate of 50 kg/hr (triangle); co-spray dried mannitol:sorbitol placebo having a feed rate of 75 kg/hr ("X"); dry blend of spray-dried mannitol and crystalline sorbitol placebo (square).

FIG. 7 illustrates the results of a compactibility study on placebo tablets prepared according to Example 5 and produced by co-spray drying with dry seeding using various dry-feed rates. Lower compression forces produce tablets with increased hardness, and the dry feed rate seemed to have no effect on tablet hardness. Each feed rate produced a similar, steep curve. For example, a feed rate of 12.5 kg/hr at a compression force of 8 KN produced a tablet having a harness of about 8.0 KP. A feed rate of 50 kg/hr at the same compression force produced a tablet having a hardness of about 8.5 KP. A feed rate of 75 kg/hr also produced a tablet having a hardness of about 8 KP at the same compression force. Each of the formulations which were seeded with a dry blend produced a tablet having at least a hardness of 11 KP before reaching a compression force of 10 KN. The control formulation produced a tablet having a hardness of about 4 KP at a compression force of 8 KN, and at 10 KN produced a tablet having a hardness of about 6 KP.

Figure 8:
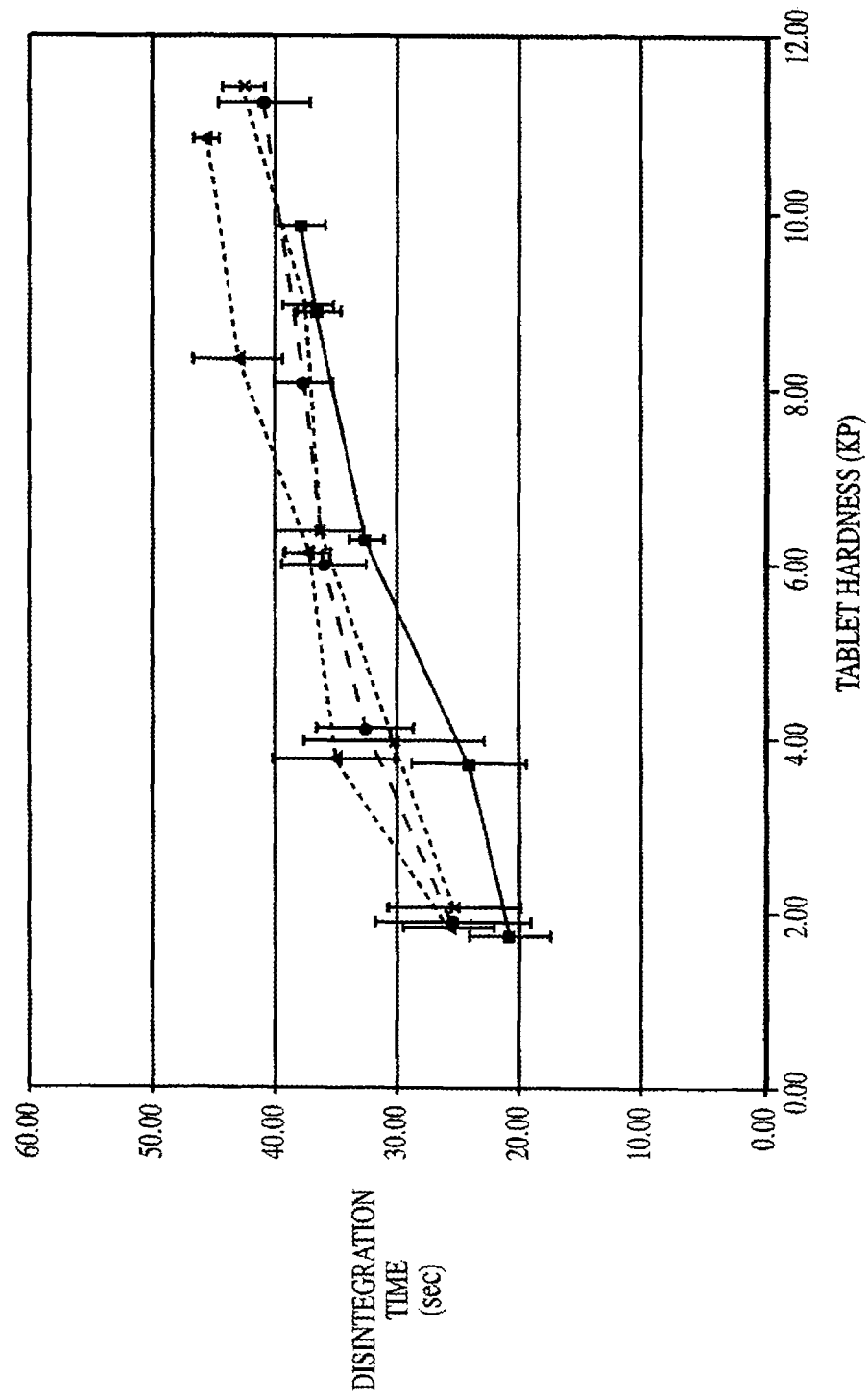
FIG. 8 is a graph illustrating in-vivo disintegration times for the formulations in the description for FIG. 7. The data is represented according to the legend in FIG. 7.
Figure 9A:
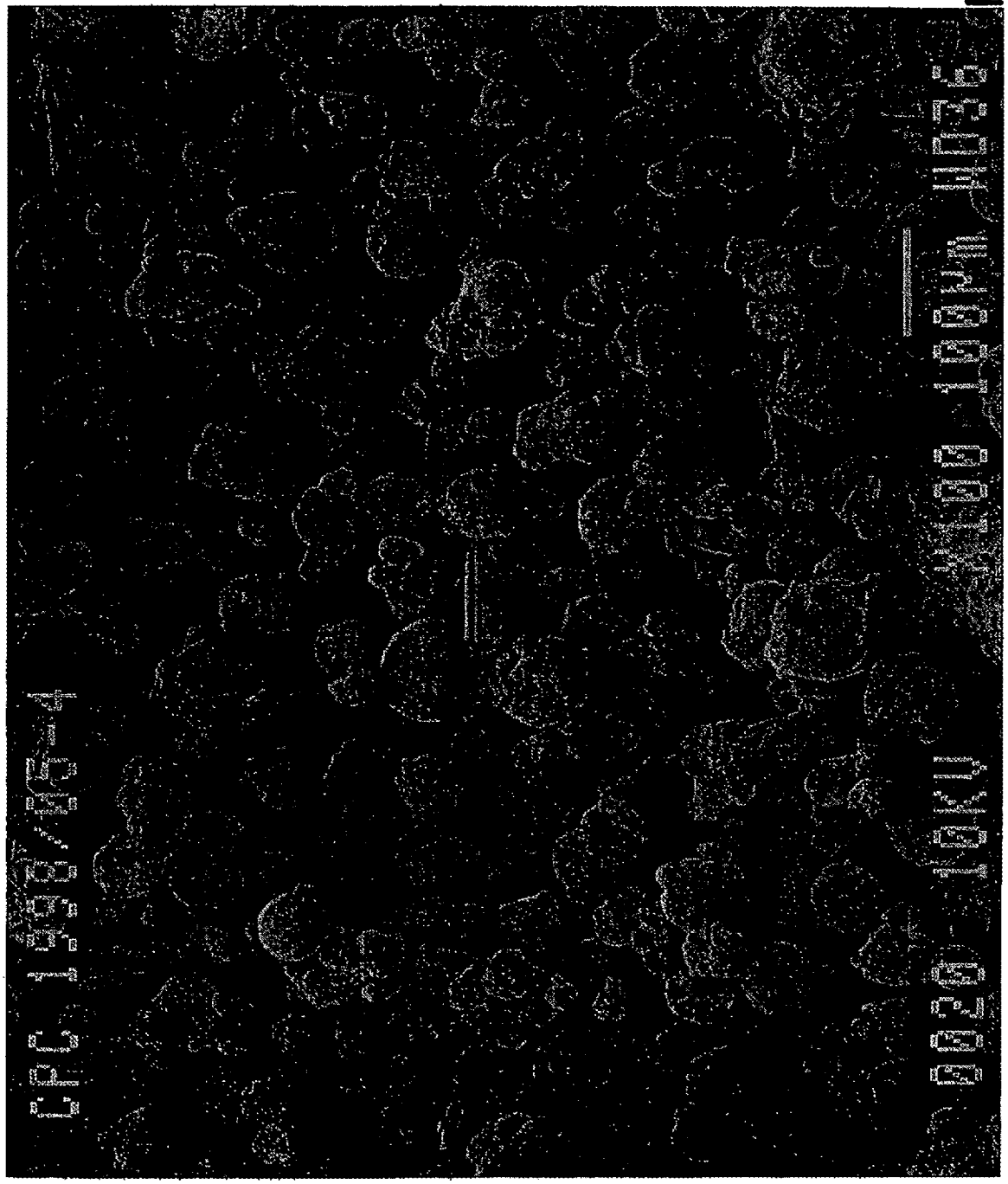
FIGS. 9A, 9B, and 9C include a set of SEMs illustrating the morphology of the particles produced by co-spray drying a mannitol:sorbitol mixture combined with seeding with a dry blend of mannitol:sorbitol in the same ratio during the spray-drying process according to one aspect of the present invention. The dry-feed rate used to produce the particles in FIGS. 9A-9C was 12.5 kg/hr.
Figure 9B:
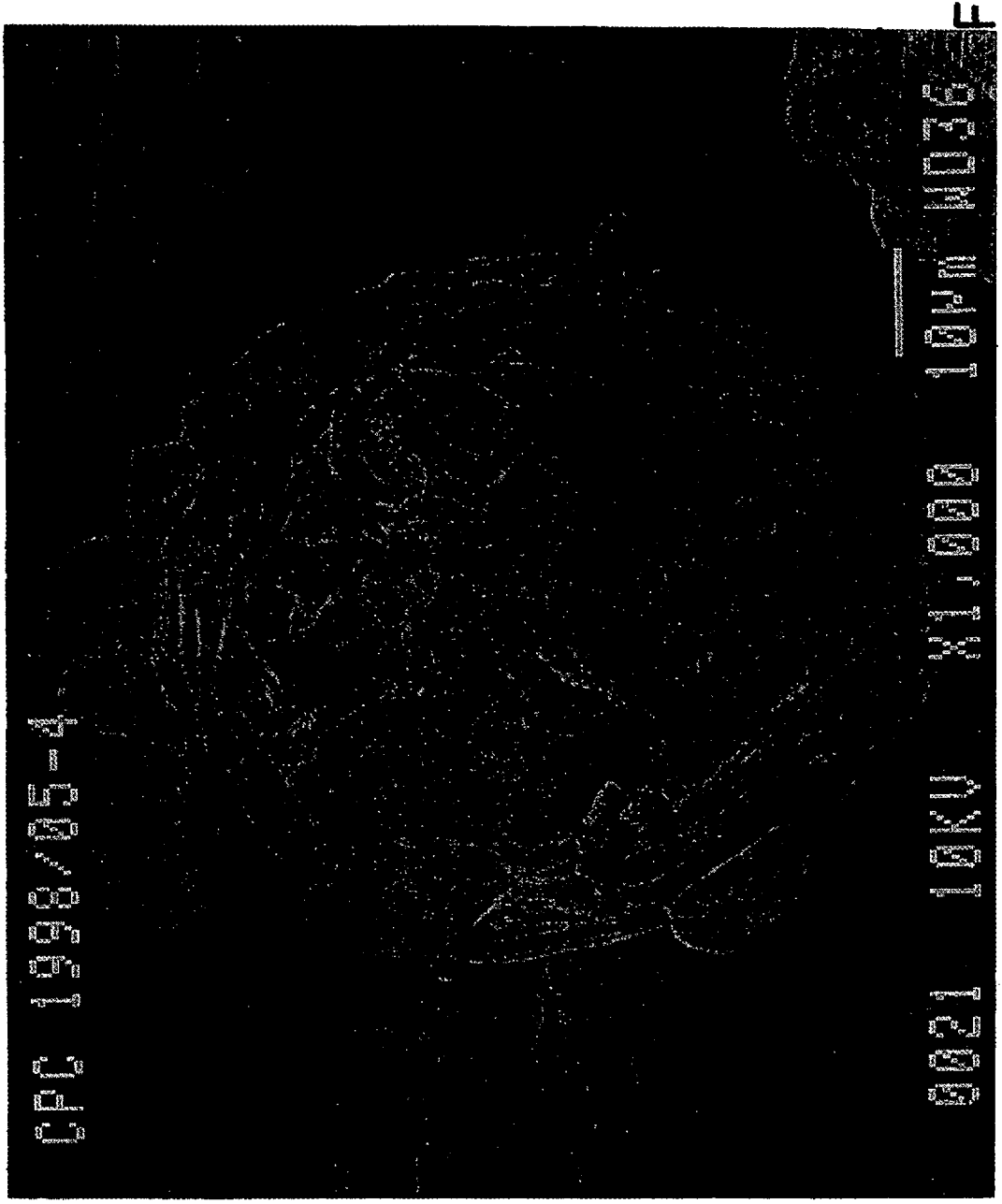
Figure 9C:
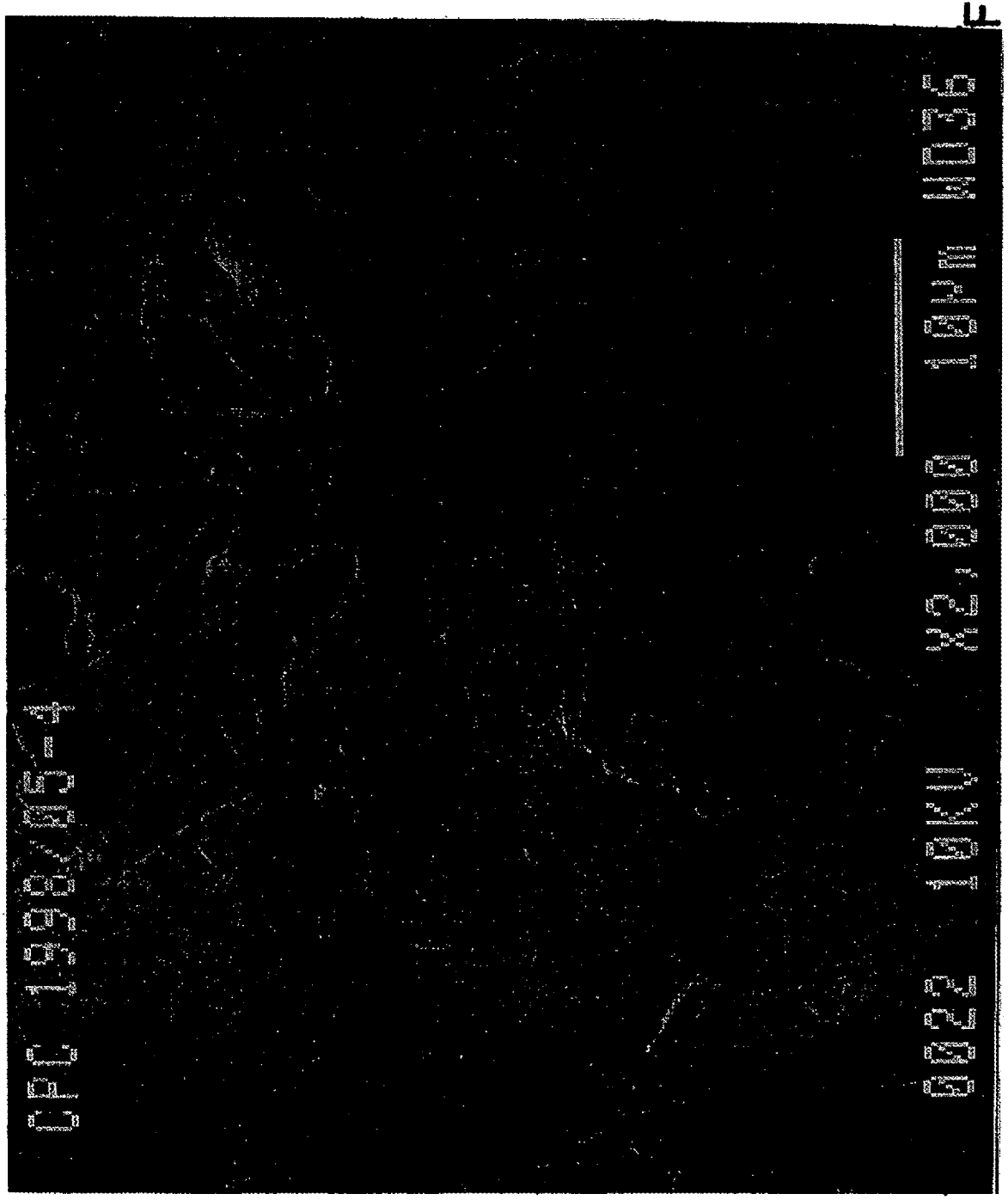
Figure 10A:
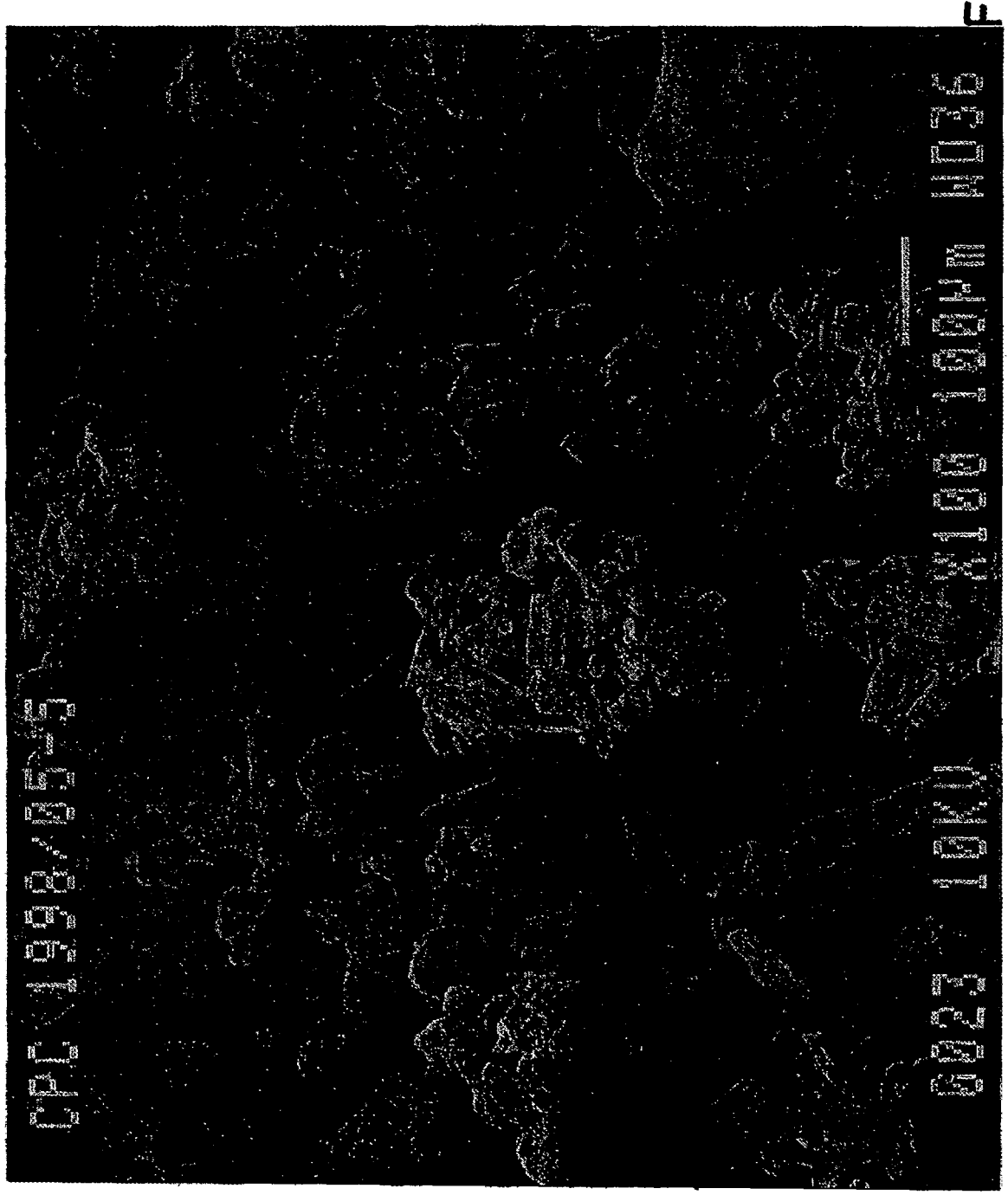
FIGS. 10A, 10B, and 10C include a set of SEMs illustrating the morphology of the particles produced by co-spray drying a mannitol:sorbitol mixture combined with seeding with a dry blend of mannitol:sorbitol in the same ratio during the spray-drying process according to one aspect of the present invention. The dry-feed rate used to produce the particles in FIGS. 10A-10C was 75 kg/hr.
Figure 10B:
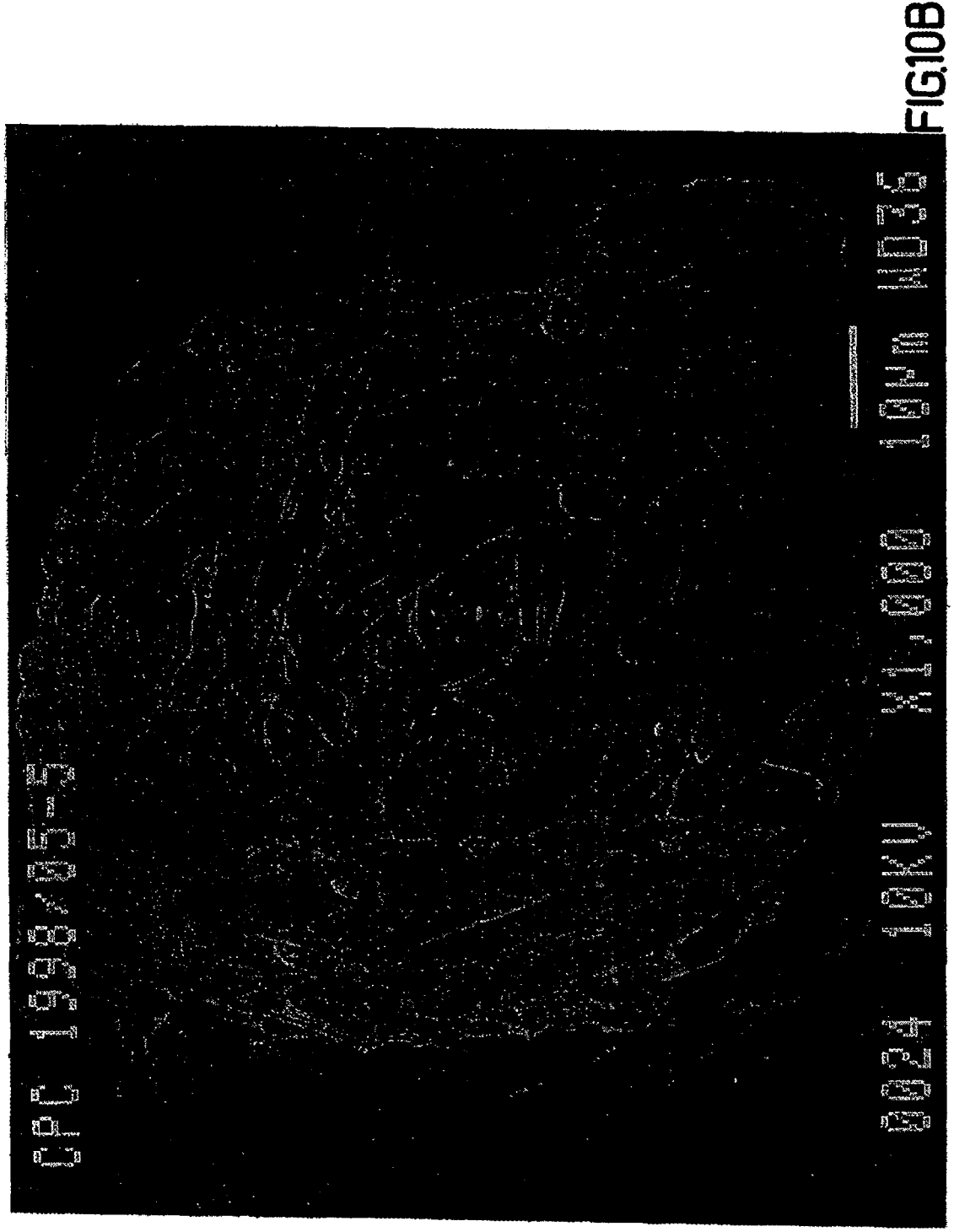
Figure 10C:
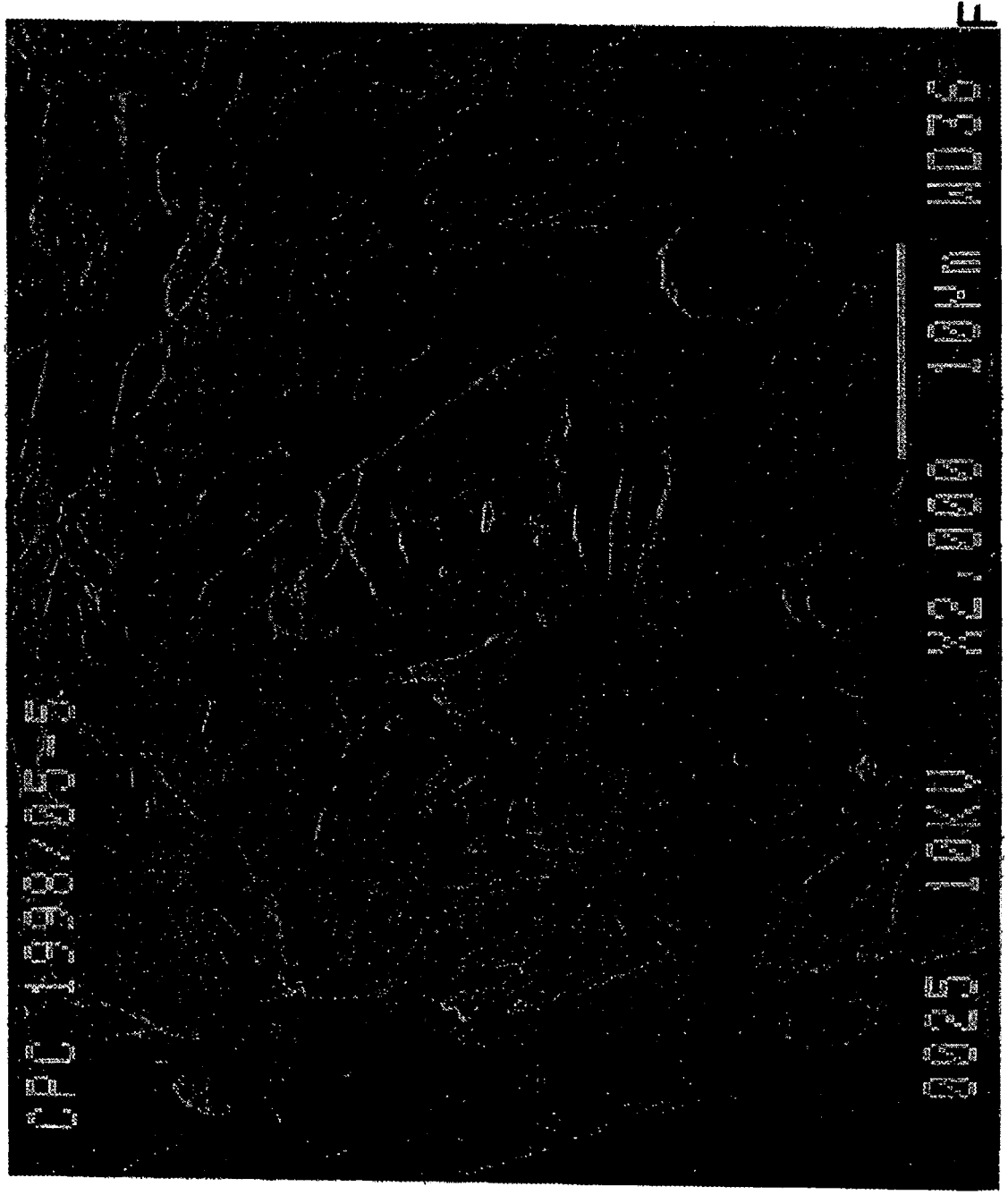

FIG. 8 illustrates the results of an in-vivo disintegration time study on tablets prepared according to Example 5 and produced by co-spray drying with dry seeding using various dry-feed rates. Again, dry-feed rates seemed to have no effect on in vivo disintegration times. As tablet hardness increased, disintegration time increased slightly. However, even with a tablet hardness of around 11 KP, disintegration times for each formulation were still less than 50 seconds. At all tablet hardness points, the control formulation without dry seeding disintegrated in less time, however, these differences in disintegration time do not seem to be significant as indicated by the error bars.

Comparing FIG. 8 and FIG. 3, the in vivo disintegration times appear to be slightly enhanced by the addition of the dry-blend during the co-spray drying process. In both Formulation A (90:10 mannitol:sorbitol) and Formulation D (80:20 mannitol:sorbitol) of FIG. 3 (no dry-blend addition), the in vivo disintegration time exceed 50 seconds at a tablet hardness of 8 KP, while in FIG. 8, the in vivo disintegration times range between 38 and 44 seconds at 8 KP for each of the formulations with a dry-blend added at different dry feed rates.

FIGS. 9A-9C and 10A-10C are SEMs of the particles produced by seeding with a dry-blend of mannitol:sorbitol in the same ratio used for co-spray drying. The dry feed rate used in the experiment which produced the particles shown in FIGS. 9A-9C and 10A-10C were 12.5 kg/hr and 75 kg/hr, respectively. There was no significant difference in the morphology of these particles. The particles continue to be spherical and little or no filamentous structure is observed on the surface of the particles.

It has been concluded that the dry-feed rate does not impact the morphology of the resulting particle; the quick dissolve aspects of the tablets produced from particles seeded with dry-blends of mannitol:sorbitol have been enhanced by the addition of the dry-blend in the co-spray drying process, as indicated by the decrease in in-vivo disintegration time.

Example 7

Dilution of the Co-Processed Product with MANNOGEM EZ™ and POLYPLASDONE XL™

Formulations were prepared as in Experiment 6. Two additional formulations were prepared as described in Experiment 6, using a dry feed rate of about 37.5 kg/hr for "seeding." These additional formulations were diluted after the co-spray drying process with either 20% or 40% of a mixture of about 90% MANNOGEM EZ™ and about 10% POLYPLASDONE-XL™ ("EZ/XL"). In-vivo disintegration time, compactibility, and friability were measured for each of the formulations.

Figure 11:
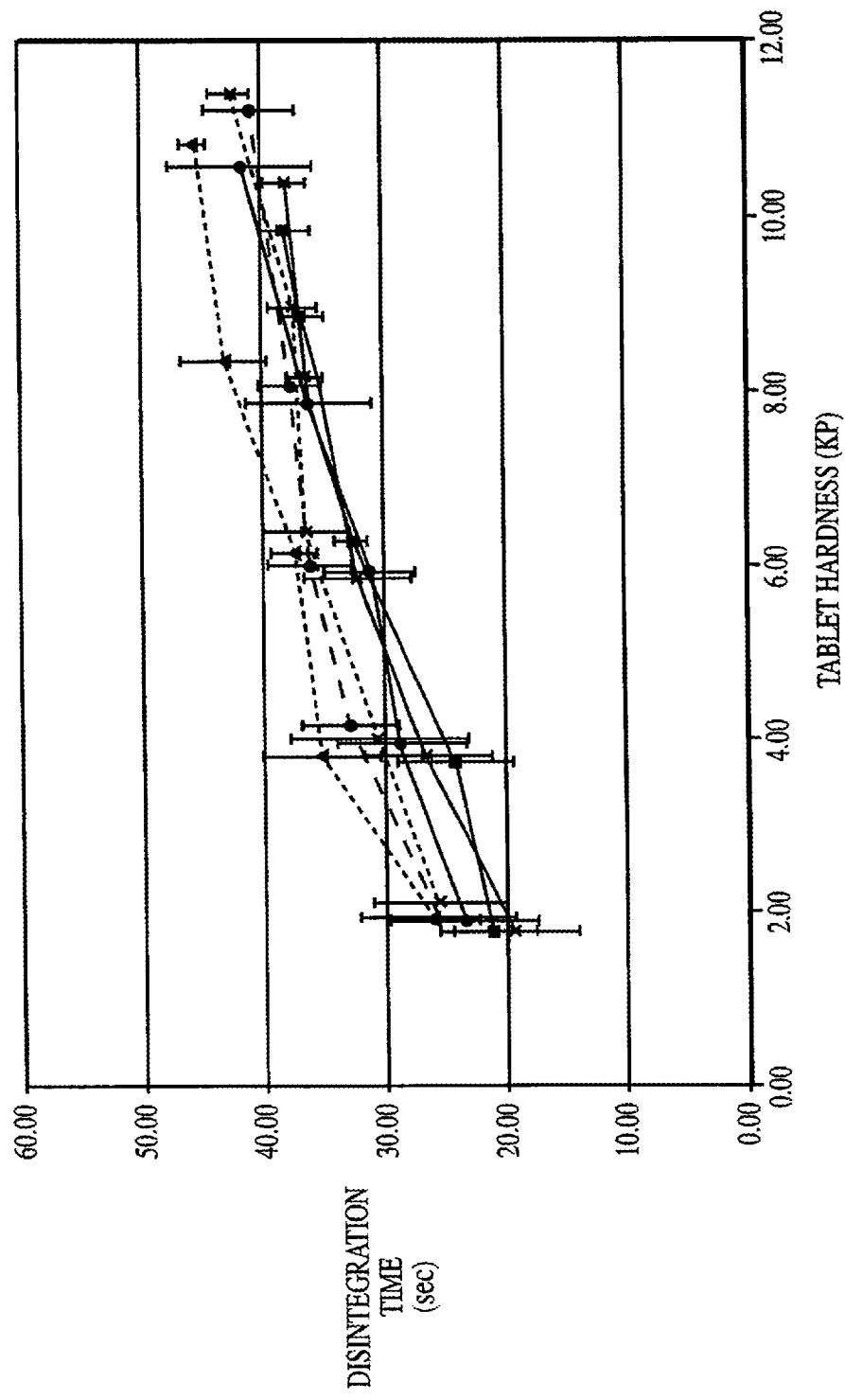
FIG. 11 is a graph depicting the in-vivo disintegration time for different placebo formulations of co-spray dried mannitol:sorbitol mixtures seeded with dry blends of mannitol:sorbitol in the same ratio at varying feed rates, and optionally, followed by a dilution of the product with a percentage of a mixture of MANNOGEM EZ™ (SPI Polyols, Inc., New Castle, Del.) and POLYPLASDONE XL™ (ISP Technologies, Wayne, N.J.; "EZ/XL"). Data is represented as follows: co-spray dried mannitol:sorbitol placebo having a feed rate of 50 kg/hr (triangle); co-spray dried mannitol:sorbitol placebo having a feed rate of 12.5 kg/hr (circle, dashed line); co-spray dried mannitol:sorbitol placebo having a feed rate of 75 kg/hr ("X" dashed line); co-spray dried mannitol:sorbitol placebo having a feed rate of 37.5 kg/hr and diluted with 20% EZ/XL (asterisk, solid line); co-spray dried mannitol:sorbitol placebo having a feed rate of 37.5 kg/hr and diluted with 40% EZ/XL (circle, solid line); and dry blend of spray-dried mannitol and crystalline sorbitol placebo (square).

FIG. 11 graphs the results for in vivo disintegration times for each of the 5 formulations tested. The control formulation is indicated by the "square" line marker. Even at the highest tablet hardness value of about 11 KP, the disintegration time for any formulation did not exceed about 46 seconds. The formulations diluted with the EZ/XL mixture seemed to have slightly superior disintegration properties, as indicated in FIG. 11. For example, at a tablet hardness of about 8 KP, the disintegration times for both EZ/XL formulations were slightly lower (about 1 to 8 seconds lower) than the formulations which were not diluted. The variation in disintegration times is more pronounced at lower tablet hardness values. For example, at a tablet hardness of about 4 KP, the EZ/XL formulations disintegrated in about 26 to 28 seconds, while the other formulations took about 30 to 35 seconds to disintegrate. The control formulation disintegrated in about 24 seconds. Thus, it was concluded that the EZ/XL formulations increase the quick-dissolve properties of the basic formulations.

Figure 12:
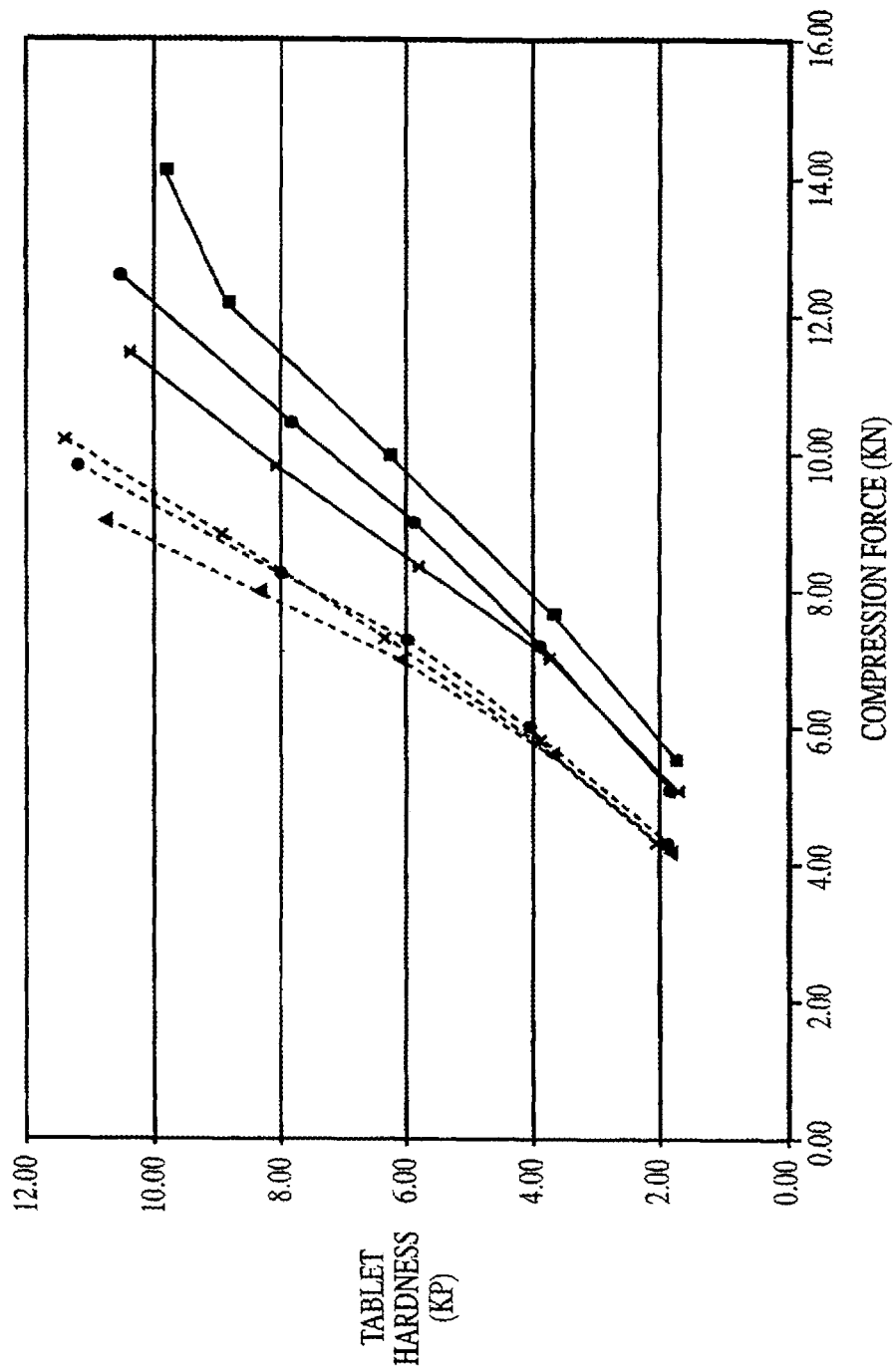
FIG. 12 is a graph depicting compactibility for different placebo formulations as described in FIG. 11. The legend for the graph is the same as the legend described in FIG. 11.

FIG. 12 illustrates the compaction profile for each of the 5 formulations and the control. Each of the seeded formulations had a maximum compression force of about 8.5 KN to about 10 KN, which produced a tablet having a hardness of about 10.8 KP to 11.5 KP. The EZ/XL formulations had a maximum compression force of about 10 KN to 12 KN, which produced a tablet having a hardness of about 10.3 KN to about 10.5 KN. The control formulation displayed a maximum compression force of about 14 KN, which produced a tablet having a hardness of about 10 KN. Thus, it was concluded that the dilution process formed a tablet with superior compaction properties as compared with the control tablet.

Figure 13:
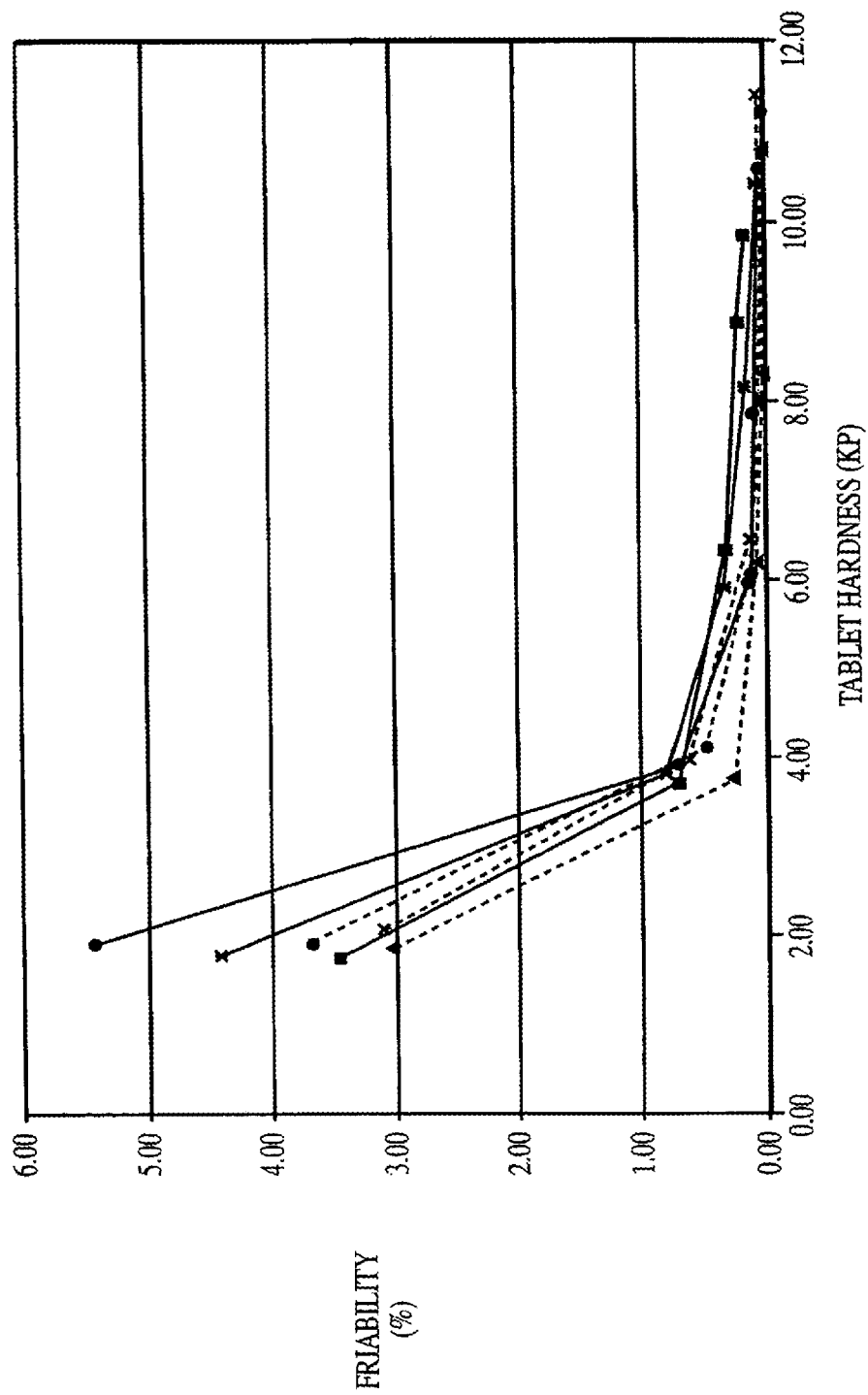
FIG. 13 is a graph depicting friability for different placebo formulations as described in FIG. 11. The legend for the graph is the same as the legend described in FIG. 11.

FIG. 13 illustrates the percent friability for each of the 5 formulations and the control. The percent friability for all of the formulations approached zero at a tablet hardness of about 6 KP. At a tablet hardness of about 4 KP, all of the formulations had a percent friability of about 0.5 to about 0.7, with the exception of the co-spray dried formulation seeded at a feed rate of about 50 kg/hr, which had a percent friability of about 0.25. It was concluded that the dilution of the co-spray dried formulations with the EZ/XL mixture had no significant effect on the friability of the tablet produced from those formulations. Thus, in vivo disintegration time can be decreased while having no effect on friability.

The dilution process represents a viable alternative to simply co-spray drying since it appeared to have little or no effect on friability, it decreases in vivo disintegration time, and the compaction profile is superior to the control profile.

Example 8

Quick Dissolve Preparations Comprising Spray-Dried Mannitol

A quick dissolving preparation according to the present invention, in the form of tablets, was produced as set forth below.

A mixture of 2.0 kg of MANNOGEM™ EZ (SPI Pharma, New Castle, Del.), 0.23 kg of silica gel (SYLOID®244FP, W.R. Grace & Co., Grace Davidson, Columbia, Md.) and 0.23 kg of colloidal silica (Cab-O-Sil M-5, obtained from Cabot Corp., Tuscola, Ill.) was created by adding the components to two polyethylene bags which were then shaken for about five (5) minutes.

The mixture was then discharged to a 10 cubic foot V-blender (Patterson-Kelly 10 cubic foot) along with the following additional materials: 103.78 kg MANNOGEM EZ™ (added in two approximately equal parts), 5.63 kg of POLYPASDONE XL-10™ (ISP Technologies, 1361 Alps Road, Wayne, N.J. 07470), 3.75 kg of sodium croscarmellose (Ac-Di-Sol®, FMC Bio polymer, Newark, Del.), and 9.38 kg of Starch 1500 (Colorcon, West Point, Pa.). The blender was than started and the contents of the blender were blended for 20 minutes at a moderate speed (about 6-20 RPM) to form an initial mixture.

After the blending step, the contents of the blender were discharged into containers.

In some instances, it may be necessary to de-lump the ingredients, for example by passing the ingredients through a screening step (e.g., using 20 or 30 mesh screens) before they are added to the blender. This is especially true for the MANNOGEM EZ™, which should be checked for lumps or large agglomerates before it is added to the blender.

A tableting mixture was prepared by adding 1024.5 grams of the initial mixture, 226.1 grams of acetaminophen (Eurand Acetaminophen microcaps, Vandalia, Ohio), 13 grams of peppermint flavor (FONA 894.022, Carol Stream, Ill.), 6.5 grams of menthol flavor (FONA 875.008.5 Carol Stream, Ill.); 1.95 grams of aspartame (Aspartame, Nutrasweet, Augusta, Ga.) to a two liter glass vessel (Turbula T2C and blended for 15 minutes at 30 rpm. After the 15 minute blending step, 13 grams of magnesium stearate (Mallinckrodt, St. Louis, Mo.) and 13 grams of talc (Talc 140 from Mutchler, Westwood, N.J.) are added to the blender and the blender is restarted for 5 minutes at 30 rpm to form the final tableting mixture.

The final tableting mixture is transferred to the hopper of 16 station tablet press with two punches fitted (Cadmach DC-60, Key Instruments, Englishtown, N.J.) and processed into 500 mg tablets using one-half inch flat beveled edge tooling (D-Tooling half inch flat beveled edge (bisect). The tablet press speed was 22 RPM resulting in 44 tablets per minute. The final tablets were cylindrical in shape and had the following dimensions: 12.89 mm circular diameter and 3.85 mm thick. Each tablet weighed about 500 mg and contained about 86.95 mg of acetaminophen as the active ingredient. The hardness of the tablets was about 40N and the friability of the tablets (standard USP method) was about 8%. These tablets would need to be packaged in protective packages (e.g., blister packs) so that the friability would be less than 1% (in the packaged form).

It will be apparent to those skilled in the art that various modifications and variations can be made in the methods and compositions of the present invention without departing from the spirit or scope of the invention. Thus, it is intended that the present invention cover the modifications and variations of the present invention provided they come within the scope of the appended claims and their equivalents.

What is claimed is:

1. A method for producing a directly compressible and highly compactible composition, said method comprising:
   dissolving mannitol powder and sorbitol powder into a solution;
   seeding the solution with a blend of co-spray-dried particles consisting essentially of mannitol and sorbitol, wherein the ratio of mannitol powder to sorbitol powder in the solution is the same as the ratio of mannitol to sorbitol in the blend of dry particles;
   drying the solution in an air stream; and
   forming particles having a nonfilamentous microstructure from the solution.

2. The method of claim 1, further comprising adding a disintegrant to the composition.

3. The method of claim 2, wherein the disintegrant is selected from the group consisting of crospovidone, croscarmellose, sodium starch glycolate, and combinations thereof.

4. The method of claim 2, further comprising adding a glidant to the composition.

5. The method of claim 4, wherein the glidant is selected from the group consisting of colloidal silica, silica gel, precipitated silica, and combinations thereof.

6. The method of claim 1, further comprising adding an active ingredient.

7. The method of claim 1, further comprising forming a tablet comprising the particles.

8. A quick-dissolving composition comprising:
   particles having a surface with a nonfilamentous microstructure, the particles comprising (i) co-spray-dried polyols consisting essentially of sorbitol and mannitol, wherein the particles are produced by seeding a solution comprising the polyols selected in (i) with a blend of dry particles of the polyols selected in (i), wherein the ratio of the polyols in the solution is the same as the ratio of the polyols in the blend of dry particles; and
   a disintegrant,
   wherein said composition dissolves in the oral cavity in less than 60 seconds.

9. The composition of claim 8, further comprising a glidant.

10. The composition of claim 8, wherein said disintegrant is selected from the group consisting of crospovidone, croscarmellose, sodium starch glycolate, and combinations thereof.

11. The composition of claim 9, wherein said glidant is selected from group consisting of colloidal silica, silica gel, precipitated silica, and combinations thereof.

12. The composition of claim 8, wherein said polyols comprise mannitol and sorbitol, wherein said mannitol is present in a range of 60 to 99.5 percent and wherein said sorbitol is present in a range of 0.5 to 40 percent.

13. The composition of claim 12, wherein said mannitol is present in a range of 70 to 95 percent and wherein said sorbitol is present in a range of 5 to 30 percent.

14. The composition of claim 13, wherein said mannitol is present in a range of 80 to 90 percent and wherein said sorbitol is present in a range of 10 to 20 percent.

15. The composition of claim 8, further comprising an active ingredient.

16. The composition of claim 15, wherein said active ingredient is coated.

17. The composition of claim 15, wherein said active ingredient is uncoated.

18. The composition of claim 8, wherein said composition is directly compressible.

19. A tablet comprising the composition of claim 8.

20. A composition comprising:
   (a) particles including co-spray dried mannitol and sorbitol, wherein the particles are produced by seeding a solution comprising mannitol and sorbitol with a blend of dry particles consisting essentially of mannitol and sorbitol, wherein the ratio of the mannitol to the sorbitol in the solution is the same as the ratio of the mannitol to the sorbitol in the blend of dry particles; wherein the particles have a nonfilamentous microstructure;
   (b) a disintegrant selected from the group consisting of crospovidone, croscarmellose, sodium starch glycolate, and combinations thereof;
   (c) a glidant selected from the group consisting of silica gel, colloidal silica, precipitated silica, and combinations thereof; and
   (d) an active ingredient.

* * * * *